US011583327B2

(12) United States Patent
McHale et al.

(10) Patent No.: US 11,583,327 B2
(45) Date of Patent: Feb. 21, 2023

(54) MINIMALLY INVASIVE INTERBODY FUSION

(71) Applicant: Spinal Elements, Inc., Carlsbad, CA (US)

(72) Inventors: Patricia McHale, Mountain View, CA (US); James K. Lee, Castro Valley, CA (US); Douglas M. Lorang, San Jose, CA (US); Laurent B. Schaller, Los Altos, CA (US); Sandeep Kunwar, Woodside, CA (US); Richard G. Fessler, Winnetka, IL (US); Frederick Serrahsu, Fremont, CA (US); Helson Pacheco-Serrant, El Paso, TX (US)

(73) Assignee: Spinal Elements, Inc., Carlsbad, CA (US)

( * ) Notice: Subject to any disclaimer, the term of this patent is extended or adjusted under 35 U.S.C. 154(b) by 232 days.

(21) Appl. No.: 16/965,028

(22) PCT Filed: Jan. 28, 2019

(86) PCT No.: PCT/US2019/015386
§ 371 (c)(1),
(2) Date: Jul. 27, 2020

(87) PCT Pub. No.: WO2019/148083
PCT Pub. Date: Aug. 1, 2019

(65) Prior Publication Data
US 2020/0345401 A1 Nov. 5, 2020

Related U.S. Application Data

(60) Provisional application No. 62/718,570, filed on Aug. 14, 2018, provisional application No. 62/623,025, filed on Jan. 29, 2018.

(51) Int. Cl.
*A61B 17/88* (2006.01)
*A61B 90/00* (2016.01)
(Continued)

(52) U.S. Cl.
CPC ...... *A61B 17/8852* (2013.01); *A61B 2017/00526* (2013.01); *A61B 2017/00867* (2013.01); *A61B 2090/3966* (2016.02); *A61F 2/4465* (2013.01)

(58) Field of Classification Search
CPC ....... A61B 17/88; A61B 17/8852; A61F 2/44; A61F 2/4455; A61F 2/442; A61F 2/46; A61F 2/4601; A61F 2/4611
See application file for complete search history.

(56) References Cited

U.S. PATENT DOCUMENTS

| 2,002,021 A | 5/1935 | Rouse |
| 3,807,390 A | 4/1974 | Ostrowski et al. |

(Continued)

FOREIGN PATENT DOCUMENTS

| DE | 42 22 121 | 9/1993 |
| DE | 197 10 392 | 7/1999 |

(Continued)

OTHER PUBLICATIONS

Official Communication in European Application No. 08730402.8, dated Feb. 18, 2013.
(Continued)

*Primary Examiner* — Christopher J Beccia
(74) *Attorney, Agent, or Firm* — Knobbe, Martens, Olson & Bear, LLP

(57) ABSTRACT

Methods and apparatus are disclosed for distracting tissue. The devices and methods may include insertion of first and second elongated members into the space between two tissue layers, with an augmenting elongated member at least partially inserted therebetween to form a distraction device
(Continued)

between the tissues to be distracted. At least one of the first and second elongated members may be formed of a flexible core member with a plurality of rigid veneer members spaced along the length of the core member. At least one of the elongated members may include a shaping member that automatically moves from a generally linear configuration to a generally less linear configuration. A deployment catheter may include a deformable distal end to allow augmentation of the tissue distraction device during implantation. An injection aid may be provided for introducing a filler material into an interior defined by a deployed tissue distraction device.

21 Claims, 15 Drawing Sheets

(51) Int. Cl.
*A61B 17/00* (2006.01)
*A61F 2/44* (2006.01)

(56) References Cited

U.S. PATENT DOCUMENTS

| | | |
|---|---|---|
| 4,846,175 A | 7/1989 | Frimberger |
| 4,862,891 A | 9/1989 | Smithp |
| 4,863,476 A | 9/1989 | Shepperd |
| 4,898,161 A | 2/1990 | Grundei |
| 5,059,193 A | 10/1991 | Kuslich |
| 5,129,889 A | 7/1992 | Hahn et al. |
| 5,192,327 A | 3/1993 | Brantigan |
| 5,201,742 A | 4/1993 | Hasson |
| 5,219,358 A | 6/1993 | Bendel et al. |
| 5,267,994 A | 12/1993 | Gentelia et al. |
| 5,306,310 A | 4/1994 | Siebels |
| 5,342,394 A | 8/1994 | Matsuno et al. |
| 5,345,945 A | 9/1994 | Hodgson et al. |
| 5,366,490 A | 11/1994 | Edwards et al. |
| 5,374,267 A | 12/1994 | Siegal |
| 5,383,884 A | 1/1995 | Summers |
| 5,397,304 A | 3/1995 | Truckai |
| 5,397,364 A | 3/1995 | Kozak et al. |
| 5,423,806 A | 6/1995 | Dale et al. |
| 5,433,739 A | 7/1995 | Sluijter et al. |
| 5,445,639 A | 8/1995 | Kuslich et al. |
| 5,470,043 A | 11/1995 | Marts et al. |
| 5,487,757 A | 1/1996 | Truckai et al. |
| 5,500,012 A | 3/1996 | Brucker et al. |
| 5,540,696 A | 7/1996 | Booth, Jr. et al. |
| 5,549,679 A | 8/1996 | Kuslich |
| 5,554,163 A | 9/1996 | Shturman |
| 5,571,147 A | 11/1996 | Sluijter et al. |
| 5,571,189 A | 11/1996 | Kuslich |
| 5,599,346 A | 2/1997 | Edwards et al. |
| 5,697,909 A | 12/1997 | Eggers et al. |
| 5,716,416 A | 2/1998 | Lin |
| 5,718,707 A | 2/1998 | Mikhail |
| 5,755,661 A | 5/1998 | Schwartzman |
| 5,755,732 A | 5/1998 | Green et al. |
| 5,755,797 A | 5/1998 | Baumgartner |
| 5,782,832 A | 7/1998 | Larsen et al. |
| 5,788,713 A | 8/1998 | Dubach et al. |
| 5,851,214 A | 12/1998 | Larsen et al. |
| 5,871,501 A | 2/1999 | Leschinsky et al. |
| 5,885,217 A | 3/1999 | Gisselberg et al. |
| 5,916,166 A | 6/1999 | Reiss et al. |
| 5,919,235 A | 7/1999 | Husson et al. |
| 5,980,471 A | 11/1999 | Jafari |
| 5,980,504 A | 11/1999 | Sharkey et al. |
| 6,007,570 A | 12/1999 | Sharkey et al. |
| 6,019,765 A | 2/2000 | Thornhill et al. |
| 6,039,761 A | 3/2000 | Li et al. |
| 6,059,829 A | 5/2000 | Schlapfer et al. |
| 6,099,514 A | 8/2000 | Sharkey et al. |
| 6,126,660 A | 10/2000 | Dietz |
| 6,126,682 A | 10/2000 | Sharkey et al. |
| 6,183,517 B1 | 2/2001 | Suddaby |
| 6,224,630 B1 | 5/2001 | Bao et al. |
| 6,228,022 B1 | 5/2001 | Friesem et al. |
| 6,231,609 B1 | 5/2001 | Mehdizadeh |
| 6,245,072 B1 | 6/2001 | Zdeblick |
| 6,245,107 B1 | 6/2001 | Ferree |
| 6,277,112 B1 | 8/2001 | Underwood et al. |
| 6,332,895 B1 | 12/2001 | Suddaby |
| 6,375,635 B1 | 4/2002 | Moutafis et al. |
| 6,375,682 B1 | 4/2002 | Fleischmann et al. |
| 6,387,130 B1 | 5/2002 | Stone et al. |
| 6,409,766 B1 | 6/2002 | Brett |
| 6,419,704 B1 | 7/2002 | Ferree |
| 6,436,142 B1 | 8/2002 | Paes et al. |
| 6,454,806 B1 | 9/2002 | Cohen et al. |
| 6,468,270 B1 | 10/2002 | Hovda et al. |
| 6,488,710 B2 | 12/2002 | Besselink |
| 6,491,690 B1 | 12/2002 | Goble et al. |
| 6,500,205 B1 | 12/2002 | Michelson |
| 6,530,926 B1 | 3/2003 | Davison |
| 6,551,319 B2 | 4/2003 | Lieberman |
| 6,554,833 B2 | 4/2003 | Levy et al. |
| 6,558,383 B2 | 5/2003 | Cunningham et al. |
| 6,558,386 B1 | 5/2003 | Cragg |
| 6,558,390 B2 | 5/2003 | Cragg |
| 6,562,033 B2 | 5/2003 | Shah et al. |
| 6,582,431 B1 | 6/2003 | Ray |
| 6,592,625 B2 | 7/2003 | Cauthen |
| 6,595,998 B2 | 7/2003 | Johnson et al. |
| 6,602,248 B1 | 8/2003 | Sharps et al. |
| 6,607,505 B1 | 8/2003 | Thompson et al. |
| 6,607,530 B1 | 8/2003 | Carl et al. |
| 6,620,196 B1 | 9/2003 | Trieu |
| 6,656,178 B1 | 12/2003 | Veldhuizen et al. |
| 6,670,505 B1 | 12/2003 | Collins et al. |
| 6,676,665 B2 | 1/2004 | Foley et al. |
| 6,714,822 B2 | 3/2004 | King et al. |
| 6,726,684 B1 | 4/2004 | Woloszko et al. |
| 6,733,496 B2 | 5/2004 | Sharkey et al. |
| 6,749,605 B2 | 6/2004 | Ashley et al. |
| 6,764,491 B2 | 7/2004 | Frey et al. |
| 6,767,347 B2 | 7/2004 | Sharkey et al. |
| 6,773,432 B1 | 8/2004 | Clayman et al. |
| 6,821,276 B2 | 11/2004 | Lambrecht et al. |
| 6,830,570 B1 | 12/2004 | Frey et al. |
| 6,878,155 B2 | 4/2005 | Sharkey et al. |
| 6,923,811 B1 | 8/2005 | Carl et al. |
| 6,939,351 B2 | 9/2005 | Eckman |
| 6,953,458 B2 | 10/2005 | Loeb |
| 6,964,667 B2 | 11/2005 | Shaolian et al. |
| 6,976,949 B2 | 12/2005 | Winkler et al. |
| 7,004,970 B2 | 2/2006 | Cauthen III et al. |
| 7,008,432 B2 | 3/2006 | Schlapfer et al. |
| 7,025,765 B2 | 4/2006 | Balbierz et al. |
| 7,052,516 B2 | 5/2006 | Cauthen, III et al. |
| 7,056,321 B2 | 6/2006 | Pagliuca et al. |
| 7,069,087 B2 | 6/2006 | Sharkey et al. |
| 7,087,055 B2 | 8/2006 | Lim et al. |
| 7,087,058 B2 | 8/2006 | Cragg |
| 7,114,501 B2 | 10/2006 | Johnson et al. |
| 7,124,761 B2 | 10/2006 | Lambrecht et al. |
| 7,144,397 B2 | 12/2006 | Lambrecht et al. |
| 7,179,225 B2 | 2/2007 | Shluzas et al. |
| 7,204,853 B2 | 4/2007 | Gordon et al. |
| 7,211,055 B2 | 5/2007 | Diederich et al. |
| 7,241,297 B2 | 7/2007 | Shaolian et al. |
| 7,252,686 B2 | 8/2007 | Garrison et al. |
| 7,267,687 B2 | 9/2007 | McGuckin, Jr. |
| 7,282,020 B2 | 10/2007 | Kaplan |
| 7,309,336 B2 | 12/2007 | Ashley et al. |
| 7,318,823 B2 | 1/2008 | Sharps et al. |
| 7,318,826 B2 | 1/2008 | Teitelbaum et al. |
| 7,322,962 B2 | 1/2008 | Forrest |
| 7,331,956 B2 | 2/2008 | Hovda et al. |
| 7,331,963 B2 | 2/2008 | Bryan et al. |
| RE40,156 E | 3/2008 | Sharps et al. |
| 7,618,458 B2 | 11/2009 | Biedermann et al. |

(56) References Cited

U.S. PATENT DOCUMENTS

| | | |
|---|---|---|
| 7,682,378 B2 | 3/2010 | Truckai et al. |
| 7,753,912 B2 | 7/2010 | Raymond et al. |
| 7,758,647 B2 | 7/2010 | Arnin et al. |
| 7,771,432 B2 | 8/2010 | Schwab et al. |
| 7,776,051 B2 | 8/2010 | Colleran et al. |
| 7,824,445 B2 | 11/2010 | Biro et al. |
| 7,887,568 B2 | 2/2011 | Ahlgren |
| 7,901,460 B2 | 3/2011 | Sherman |
| 7,922,767 B2 | 4/2011 | Sack et al. |
| 7,947,078 B2 | 5/2011 | Siegal |
| 7,963,915 B2 | 6/2011 | Bleich |
| 8,021,429 B2 | 9/2011 | Viker |
| 8,025,697 B2 | 9/2011 | McClellan, III et al. |
| 8,083,796 B1 | 12/2011 | Raiszadeh et al. |
| 8,123,750 B2 | 2/2012 | Norton et al. |
| 8,128,662 B2 | 3/2012 | Altarac et al. |
| 8,137,401 B2 | 3/2012 | Stad et al. |
| 8,142,507 B2 | 3/2012 | McGuckin, Jr. |
| 8,246,622 B2 | 8/2012 | Siegal et al. |
| 8,252,001 B2 | 8/2012 | Quimo et al. |
| 8,252,054 B2 | 8/2012 | Greenhalgh et al. |
| 8,377,070 B2 | 2/2013 | Gauthier |
| 8,394,102 B2 | 3/2013 | Garabedian et al. |
| 8,454,617 B2 | 6/2013 | Schaller et al. |
| 8,454,622 B2 | 6/2013 | Blain et al. |
| 8,470,043 B2 | 6/2013 | Schaller et al. |
| 8,579,980 B2 | 11/2013 | DeLurio et al. |
| 8,591,583 B2 | 11/2013 | Schaller et al. |
| 8,628,577 B1 | 1/2014 | Jimenez |
| 8,632,591 B2 | 1/2014 | Vila et al. |
| 8,663,332 B1 | 3/2014 | To et al. |
| 8,685,031 B2 | 4/2014 | Kleiner et al. |
| 8,764,806 B2 | 7/2014 | Abdou |
| 8,906,028 B2 | 12/2014 | Kleiner |
| 8,968,408 B2 | 3/2015 | Schaller et al. |
| 8,974,464 B2 | 3/2015 | Johnson et al. |
| 8,979,860 B2 | 3/2015 | Micke et al. |
| 8,986,385 B2 | 3/2015 | Hall |
| 9,034,041 B2 | 5/2015 | Wolters et al. |
| 9,039,771 B2 | 5/2015 | Glerum et al. |
| 9,161,773 B2 | 10/2015 | Schaller et al. |
| 9,308,022 B2 | 4/2016 | Chitre et al. |
| 9,351,851 B2 | 5/2016 | Huffmaster et al. |
| 9,480,574 B2 | 11/2016 | Lee et al. |
| 9,566,170 B2 | 2/2017 | Schell et al. |
| 9,642,712 B2 | 5/2017 | Schaller et al. |
| 9,827,031 B2 | 11/2017 | Emery et al. |
| 9,955,961 B2 | 5/2018 | Huffmaster et al. |
| 10,022,243 B2 | 7/2018 | Emery et al. |
| 10,231,843 B2 | 3/2019 | Lee et al. |
| 10,258,228 B2 | 4/2019 | Genovese et al. |
| 10,285,821 B2 | 5/2019 | Schaller et al. |
| 10,314,605 B2 | 6/2019 | Huffmaster et al. |
| 10,426,629 B2 | 10/2019 | Schaller et al. |
| 10,575,963 B2 | 3/2020 | Schaller et al. |
| 10,709,577 B2 | 7/2020 | Lorang et al. |
| 10,758,286 B2 | 9/2020 | Ammerman et al. |
| 11,224,453 B2 | 1/2022 | Huffmaster et al. |
| 2001/0023348 A1 | 9/2001 | Ashley et al. |
| 2001/0029377 A1 | 10/2001 | Aebi et al. |
| 2001/0031981 A1 | 10/2001 | Evans et al. |
| 2002/0019637 A1 | 2/2002 | Frey et al. |
| 2002/0026197 A1 | 2/2002 | Foley et al. |
| 2002/0128716 A1 | 9/2002 | Cohen et al. |
| 2002/0147444 A1 | 10/2002 | Shah et al. |
| 2002/0156530 A1 | 10/2002 | Lambrecht et al. |
| 2003/0009223 A1 | 1/2003 | Fehling et al. |
| 2003/0014047 A1 | 1/2003 | Woloszko et al. |
| 2003/0040796 A1 | 2/2003 | Ferree |
| 2003/0065358 A1 | 4/2003 | Frecker et al. |
| 2003/0083747 A1 | 5/2003 | Winterbottom et al. |
| 2003/0158545 A1 | 8/2003 | Hovda et al. |
| 2003/0158553 A1 | 8/2003 | Michelson |
| 2003/0187453 A1 | 10/2003 | Schlapfer et al. |
| 2003/0204189 A1 | 10/2003 | Cragg |
| 2003/0220650 A1 | 11/2003 | Major et al. |
| 2004/0002762 A1 | 1/2004 | Hawkins |
| 2004/0010315 A1 | 1/2004 | Song |
| 2004/0015218 A1 | 1/2004 | Finch et al. |
| 2004/0024463 A1 | 2/2004 | Thomas, Jr. et al. |
| 2004/0049180 A1 | 3/2004 | Sharps et al. |
| 2004/0059333 A1 | 3/2004 | Carl et al. |
| 2004/0064144 A1 | 4/2004 | Johnson et al. |
| 2004/0073216 A1 | 4/2004 | Lieberman |
| 2004/0087994 A1 | 5/2004 | Suddaby |
| 2004/0092988 A1 | 5/2004 | Shaolian et al. |
| 2004/0102774 A1 | 5/2004 | Trieu |
| 2004/0106940 A1 | 6/2004 | Shaolian et al. |
| 2004/0116922 A1 | 6/2004 | Hovda et al. |
| 2004/0127893 A1 | 7/2004 | Hovda |
| 2004/0133280 A1 | 7/2004 | Trieu |
| 2004/0148028 A1 | 7/2004 | Ferree et al. |
| 2004/0153064 A1 | 8/2004 | Foley et al. |
| 2004/0167625 A1 | 8/2004 | Beyar et al. |
| 2004/0193158 A1 | 9/2004 | Lim et al. |
| 2004/0230198 A1 | 11/2004 | Manzi et al. |
| 2004/0230309 A1 | 11/2004 | DiMauro et al. |
| 2004/0249464 A1 | 12/2004 | Bindseil et al. |
| 2004/0260305 A1 | 12/2004 | Gorensek et al. |
| 2005/0021030 A1 | 1/2005 | Pagliuca et al. |
| 2005/0021041 A1 | 1/2005 | Michelson |
| 2005/0033292 A1 | 2/2005 | Teitelbaum et al. |
| 2005/0038517 A1 | 2/2005 | Carrison et al. |
| 2005/0049623 A1 | 3/2005 | Moore et al. |
| 2005/0065610 A1 | 3/2005 | Pisharodi |
| 2005/0070911 A1 | 3/2005 | Carrison et al. |
| 2005/0080425 A1 | 4/2005 | Bhatnagar et al. |
| 2005/0090833 A1 | 4/2005 | DiPoto |
| 2005/0090899 A1 | 4/2005 | DiPoto |
| 2005/0107878 A1 | 5/2005 | Conchy |
| 2005/0113832 A1 | 5/2005 | Molz et al. |
| 2005/0119750 A1 | 6/2005 | Studer |
| 2005/0131540 A1 | 6/2005 | Trieu |
| 2005/0131541 A1 | 6/2005 | Trieu |
| 2005/0137601 A1 | 6/2005 | Assell et al. |
| 2005/0137605 A1 | 6/2005 | Assell et al. |
| 2005/0149049 A1 | 7/2005 | Assell et al. |
| 2005/0165420 A1 | 7/2005 | Cha |
| 2005/0182414 A1 | 8/2005 | Manzi et al. |
| 2005/0182416 A1 | 8/2005 | Lim et al. |
| 2005/0187537 A1 | 8/2005 | Loeb et al. |
| 2005/0203527 A1 | 9/2005 | Carrison et al. |
| 2005/0222683 A1 | 10/2005 | Berry |
| 2005/0228391 A1 | 10/2005 | Levy et al. |
| 2005/0234493 A1 | 10/2005 | Carr et al. |
| 2005/0240171 A1 | 10/2005 | Forrest |
| 2005/0251134 A1 | 11/2005 | Woloszko et al. |
| 2005/0251177 A1 | 11/2005 | Saadat et al. |
| 2005/0256525 A1 | 11/2005 | Culbert et al. |
| 2005/0261683 A1 | 11/2005 | Veldhuizen et al. |
| 2005/0261684 A1 | 11/2005 | Shaolian et al. |
| 2005/0261692 A1 | 11/2005 | Carrison et al. |
| 2005/0273173 A1 | 12/2005 | Gordon et al. |
| 2005/0278027 A1 | 12/2005 | Hyde |
| 2005/0278036 A1 | 12/2005 | Leonard et al. |
| 2006/0015131 A1 | 1/2006 | Kierce et al. |
| 2006/0025797 A1 | 2/2006 | Lock et al. |
| 2006/0030933 A1 | 2/2006 | DeLegge et al. |
| 2006/0036241 A1 | 2/2006 | Siegal |
| 2006/0041258 A1 | 2/2006 | Galea |
| 2006/0041295 A1 | 2/2006 | Osypka |
| 2006/0047178 A1 | 3/2006 | Winkler et al. |
| 2006/0052793 A1 | 3/2006 | Heinz |
| 2006/0058826 A1 | 3/2006 | Evans et al. |
| 2006/0058876 A1 | 3/2006 | McKinley |
| 2006/0074425 A1 | 4/2006 | Sutterlin et al. |
| 2006/0085070 A1 | 4/2006 | Kim |
| 2006/0089646 A1 | 4/2006 | Bonutti |
| 2006/0116689 A1 | 6/2006 | Albans |
| 2006/0129244 A1 | 6/2006 | Ensign et al. |
| 2006/0136064 A1 | 6/2006 | Sherman |
| 2006/0149268 A1 | 7/2006 | Truckai et al. |
| 2006/0161162 A1 | 7/2006 | Lambrecht et al. |
| 2006/0178666 A1 | 8/2006 | Cosman et al. |

(56) References Cited

U.S. PATENT DOCUMENTS

| | | |
|---|---|---|
| 2006/0189999 A1 | 8/2006 | Zwirkoski |
| 2006/0195091 A1 | 8/2006 | McGraw et al. |
| 2006/0195094 A1 | 8/2006 | McGraw et al. |
| 2006/0206116 A1 | 9/2006 | Yeung |
| 2006/0217811 A1 | 9/2006 | Lambrecht et al. |
| 2006/0224154 A1 | 10/2006 | Shadduck et al. |
| 2006/0224241 A1 | 10/2006 | Butler et al. |
| 2006/0229625 A1 | 10/2006 | Truckai et al. |
| 2006/0235418 A1 | 10/2006 | Gil et al. |
| 2006/0241577 A1 | 10/2006 | Balbierz et al. |
| 2006/0247600 A1 | 11/2006 | Yeung et al. |
| 2006/0247784 A1 | 11/2006 | Kim |
| 2006/0265076 A1 | 11/2006 | Carter et al. |
| 2006/0265077 A1* | 11/2006 | Zwirkoski ............. A61F 2/4611 623/17.14 |
| 2006/0287726 A1 | 12/2006 | Segal et al. |
| 2006/0287727 A1 | 12/2006 | Segal et al. |
| 2006/0287729 A1 | 12/2006 | Segal et al. |
| 2006/0287730 A1 | 12/2006 | Segal et al. |
| 2007/0010848 A1 | 1/2007 | Leung et al. |
| 2007/0016273 A1 | 1/2007 | Scarborough et al. |
| 2007/0027545 A1 | 2/2007 | Carls et al. |
| 2007/0032791 A1 | 2/2007 | Greenhalgh |
| 2007/0050030 A1 | 3/2007 | Kim |
| 2007/0050032 A1 | 3/2007 | Gittings et al. |
| 2007/0055259 A1 | 3/2007 | Norton et al. |
| 2007/0055262 A1 | 3/2007 | Tomita et al. |
| 2007/0060935 A1 | 3/2007 | Rdt et al. |
| 2007/0067035 A1 | 3/2007 | Falahee |
| 2007/0093822 A1 | 4/2007 | Dutoit et al. |
| 2007/0093899 A1 | 4/2007 | Dutoit et al. |
| 2007/0118219 A1 | 5/2007 | Hyde |
| 2007/0123888 A1 | 5/2007 | Bleich et al. |
| 2007/0123903 A1 | 5/2007 | Raymond et al. |
| 2007/0123986 A1 | 5/2007 | Schaller et al. |
| 2007/0149978 A1 | 6/2007 | Shezifi et al. |
| 2007/0149990 A1 | 6/2007 | Palmer et al. |
| 2007/0162032 A1 | 7/2007 | Johnson et al. |
| 2007/0162062 A1 | 7/2007 | Norton et al. |
| 2007/0162127 A1 | 7/2007 | Peterman et al. |
| 2007/0162135 A1 | 7/2007 | Segal et al. |
| 2007/0168041 A1 | 7/2007 | Kadiyala |
| 2007/0168043 A1 | 7/2007 | Ferree |
| 2007/0173939 A1 | 7/2007 | Kim et al. |
| 2007/0175959 A1 | 8/2007 | Shelton, IV et al. |
| 2007/0191837 A1 | 8/2007 | Trieu |
| 2007/0198021 A1 | 8/2007 | Wales |
| 2007/0198025 A1 | 8/2007 | Trieu et al. |
| 2007/0208426 A1 | 9/2007 | Trieu |
| 2007/0213704 A1 | 9/2007 | Truckai et al. |
| 2007/0213733 A1 | 9/2007 | Bleich et al. |
| 2007/0213734 A1 | 9/2007 | Bleich et al. |
| 2007/0213735 A1 | 9/2007 | Saadat et al. |
| 2007/0225703 A1 | 9/2007 | Schmitz et al. |
| 2007/0233143 A1 | 10/2007 | Josse et al. |
| 2007/0255286 A1 | 11/2007 | Trieu |
| 2007/0255406 A1 | 11/2007 | Trieu |
| 2007/0255703 A1 | 11/2007 | Maruyama et al. |
| 2007/0260252 A1 | 11/2007 | Schmitz et al. |
| 2007/0260270 A1 | 11/2007 | Assell et al. |
| 2007/0260315 A1 | 11/2007 | Foley et al. |
| 2007/0265652 A1 | 11/2007 | Assell et al. |
| 2007/0265691 A1 | 11/2007 | Swanson |
| 2007/0276406 A1 | 11/2007 | Mahoney et al. |
| 2007/0299521 A1 | 12/2007 | Glenn et al. |
| 2008/0009826 A1 | 1/2008 | Miller et al. |
| 2008/0009828 A1 | 1/2008 | Miller et al. |
| 2008/0009847 A1 | 1/2008 | Ricart et al. |
| 2008/0009875 A1 | 1/2008 | Sankaran et al. |
| 2008/0009876 A1 | 1/2008 | Sankaran et al. |
| 2008/0009877 A1 | 1/2008 | Sankaran et al. |
| 2008/0015639 A1 | 1/2008 | Bjork et al. |
| 2008/0021435 A1 | 1/2008 | Miller et al. |
| 2008/0027407 A1 | 1/2008 | Miller et al. |
| 2008/0033465 A1 | 2/2008 | Schmitz et al. |
| 2008/0058707 A1 | 3/2008 | Ashley et al. |
| 2008/0065080 A1 | 3/2008 | Assell et al. |
| 2008/0065092 A1 | 3/2008 | Assell et al. |
| 2008/0065093 A1 | 3/2008 | Assell et al. |
| 2008/0065094 A1 | 3/2008 | Assell et al. |
| 2008/0071356 A1 | 3/2008 | Greenhalgh et al. |
| 2008/0086157 A1 | 4/2008 | Stad et al. |
| 2008/0114367 A1 | 5/2008 | Meyer |
| 2008/0147113 A1 | 6/2008 | Nobis et al. |
| 2008/0161809 A1 | 7/2008 | Schmitz et al. |
| 2008/0177259 A1 | 7/2008 | Wu |
| 2008/0183204 A1 | 7/2008 | Greenhalgh et al. |
| 2008/0221687 A1 | 9/2008 | Viker |
| 2008/0228135 A1 | 9/2008 | Snoderly |
| 2008/0234687 A1* | 9/2008 | Schaller ................ A61F 2/4425 606/90 |
| 2008/0249628 A1 | 10/2008 | Altarac et al. |
| 2008/0287995 A1 | 11/2008 | Gauthier |
| 2008/0294171 A1 | 11/2008 | Boehm, Jr. et al. |
| 2008/0300636 A1 | 12/2008 | Carli et al. |
| 2009/0012612 A1 | 1/2009 | White et al. |
| 2009/0024217 A1 | 1/2009 | Levy et al. |
| 2009/0105711 A1 | 4/2009 | Mitchell et al. |
| 2009/0143716 A1 | 6/2009 | Lowry et al. |
| 2009/0157187 A1 | 6/2009 | Richelsoph |
| 2009/0171390 A1 | 7/2009 | Sankaran |
| 2009/0198241 A1 | 8/2009 | Phan |
| 2009/0198245 A1 | 8/2009 | Phan |
| 2009/0234454 A1 | 9/2009 | Siegal |
| 2010/0030216 A1 | 2/2010 | Arcenio |
| 2010/0114179 A1 | 5/2010 | Moore et al. |
| 2010/0131005 A1 | 5/2010 | Conlon |
| 2010/0179578 A1 | 7/2010 | Tannoury et al. |
| 2010/0185291 A1 | 7/2010 | Jimenez et al. |
| 2010/0198263 A1 | 8/2010 | Siegal et al. |
| 2010/0228091 A1 | 9/2010 | Widenhouse et al. |
| 2010/0249798 A1 | 9/2010 | Sournac et al. |
| 2010/0262147 A1 | 10/2010 | Siegal et al. |
| 2010/0262242 A1 | 10/2010 | Chavatte et al. |
| 2010/0268234 A1 | 10/2010 | Aho et al. |
| 2010/0286782 A1 | 11/2010 | Schaller et al. |
| 2010/0298864 A1 | 11/2010 | Castro |
| 2011/0015638 A1 | 1/2011 | Pischl et al. |
| 2011/0015747 A1 | 1/2011 | McManus et al. |
| 2011/0112455 A1 | 5/2011 | Rocklin |
| 2011/0125266 A1 | 5/2011 | Rodgers et al. |
| 2011/0144440 A1 | 6/2011 | Cropper et al. |
| 2011/0172722 A1 | 7/2011 | Verhulst et al. |
| 2011/0208306 A1 | 8/2011 | Farris |
| 2011/0245926 A1 | 10/2011 | Kitchen |
| 2011/0307063 A1 | 12/2011 | Schaller et al. |
| 2012/0022651 A1 | 1/2012 | Akyuz et al. |
| 2012/0071977 A1 | 3/2012 | Oglaza et al. |
| 2012/0071980 A1 | 3/2012 | Purcell et al. |
| 2012/0089231 A1 | 4/2012 | Prestigiacomo |
| 2012/0123426 A1 | 5/2012 | Quimo |
| 2012/0136442 A1 | 5/2012 | Kleiner |
| 2012/0136448 A1 | 5/2012 | Seifert et al. |
| 2012/0150241 A1 | 6/2012 | Ragab et al. |
| 2012/0232664 A1 | 9/2012 | Ulrich et al. |
| 2012/0277861 A1 | 11/2012 | Steele et al. |
| 2012/0283748 A1 | 11/2012 | Ortiz et al. |
| 2012/0296171 A1 | 11/2012 | Lovell et al. |
| 2013/0053863 A1 | 2/2013 | Juravic et al. |
| 2013/0110239 A1 | 5/2013 | Siegal et al. |
| 2013/0116791 A1 | 5/2013 | Theofilos |
| 2013/0144391 A1 | 6/2013 | Siegal et al. |
| 2013/0158667 A1 | 6/2013 | Tabor et al. |
| 2013/0204374 A1 | 8/2013 | Milella, Jr. |
| 2013/0238098 A1 | 9/2013 | Schaller et al. |
| 2013/0282143 A1 | 10/2013 | Perkins et al. |
| 2013/0304070 A1 | 11/2013 | Nelson et al. |
| 2014/0058513 A1 | 2/2014 | Gahman et al. |
| 2014/0067073 A1 | 3/2014 | Hauck |
| 2014/0163326 A1 | 6/2014 | Forsell |
| 2014/0163560 A1 | 6/2014 | Fenn et al. |
| 2014/0235949 A1 | 8/2014 | Smith |
| 2014/0236296 A1 | 8/2014 | Wagner et al. |
| 2014/0249629 A1 | 9/2014 | Moskowitz et al. |

(56) References Cited

U.S. PATENT DOCUMENTS

| | | |
|---|---|---|
| 2014/0257484 A1 | 9/2014 | Flower et al. |
| 2014/0277481 A1* | 9/2014 | Lee .................. A61F 2/446 623/17.16 |
| 2014/0316427 A1 | 10/2014 | Yoon et al. |
| 2015/0012000 A1 | 1/2015 | Siegal et al. |
| 2015/0051701 A1 | 2/2015 | Glerum et al. |
| 2015/0100124 A1 | 4/2015 | Whipple |
| 2015/0112437 A1 | 4/2015 | Davis et al. |
| 2015/0112438 A1 | 4/2015 | McLean |
| 2015/0148908 A1 | 5/2015 | Marino et al. |
| 2015/0367487 A1 | 12/2015 | Nino et al. |
| 2016/0007979 A1 | 1/2016 | Bhagat et al. |
| 2016/0287409 A1 | 10/2016 | Ziemek |
| 2016/0367332 A1 | 12/2016 | Shah et al. |
| 2017/0135704 A1 | 5/2017 | Abbasi |
| 2017/0303938 A1 | 10/2017 | Rindal et al. |
| 2019/0167440 A1 | 6/2019 | Lee et al. |
| 2019/0216482 A1 | 7/2019 | Huffmaster et al. |
| 2019/0216612 A1 | 7/2019 | Schaller et al. |
| 2021/0113252 A1 | 4/2021 | Ammerman et al. |
| 2021/0154024 A1 | 5/2021 | Lorang et al. |
| 2021/0169459 A1 | 6/2021 | Pacheco-Serrant et al. |
| 2022/0031471 A1 | 2/2022 | Hessler et al. |
| 2022/0110650 A1 | 4/2022 | Huffmaster et al. |

FOREIGN PATENT DOCUMENTS

| | | |
|---|---|---|
| EP | 0 682 910 | 11/1995 |
| EP | 1 157 676 | 11/2001 |
| FR | 2 900 814 | 11/2007 |
| JP | 2002-028171 | 1/2002 |
| WO | WO 95/025485 | 9/1995 |
| WO | WO 98/017190 | 4/1998 |
| WO | WO 98/034552 | 8/1998 |
| WO | WO 99/021500 | 5/1999 |
| WO | WO 99/047058 | 9/1999 |
| WO | WO 00/074605 | 12/2000 |
| WO | WO 01/001895 | 1/2001 |
| WO | WO 03/024344 | 3/2003 |
| WO | WO 2005/048856 | 6/2005 |
| WO | WO 2006/042334 | 4/2006 |
| WO | WO 2006/047587 | 5/2006 |
| WO | WO 2006/072941 | 7/2006 |
| WO | WO 2007/009107 | 1/2007 |
| WO | WO 2007/079237 | 7/2007 |
| WO | WO 2007/100914 | 9/2007 |
| WO | WO 2008/021972 | 2/2008 |
| WO | WO 2008/036505 | 3/2008 |
| WO | WO 2008/084479 | 7/2008 |
| WO | WO 2008/103832 | 8/2008 |
| WO | WO 2008/112308 | 9/2008 |
| WO | WO 2010/008353 | 1/2010 |
| WO | WO 2011/150350 | 12/2011 |
| WO | WO 2012/048187 | 4/2012 |
| WO | WO 2012/178018 | 12/2012 |
| WO | WO 2013/043850 | 3/2013 |
| WO | WO 2014/158680 | 10/2014 |
| WO | WO 2019/148083 | 8/2019 |
| WO | WO 2019/178575 | 9/2019 |

OTHER PUBLICATIONS

International Search Report and Written Opinion in International Application No. PCT/US2008/054590, dated Aug. 22, 2008.
International Preliminary Report on Patentability and Written Opinion in International Application No. PCT/US2008/054590, dated Aug. 28, 2009.
International Search Report and Written Opinion in International Application No. PCT/US2019/015386, dated May 23, 2019.
International Preliminary Report on Patentability and Written Opinion in International Application No. PCT/US2019/015386, dated Aug. 13, 2020.
International Search Report and Written Opinion in International Application No. PCT/US2019/022632, dated May 30, 2019.
International Preliminary Report on Patentability and Written Opinion in International Application No. PCT/US2019/022632, dated Oct. 1, 2020.
International Search Report and Written Opinion in International Application No. PCT/US2014/019246, dated Aug. 19, 2014.
International Preliminary Report on Patentability and Written Opinion in International Application No. PCT/US2014/019246, dated Sep. 24, 2015.
Office Communication for U.S. Appl. No. 13/804,847, dated Jul. 13, 2015.
Office Communication for U.S. Appl. No. 13/804,847, dated Oct. 16, 2015.
Extended European Search Report for European Patent Application No. 11787510.4, dated Oct. 15, 2013.
International Search Report and Written Opinion for PCT Patent Application No. PCT/US2011/038377, dated Aug. 25, 2011.
International Search Report and Written Opinion for PCT Patent Application No. PCT/US2013/068906, dated Feb. 6, 2014.

* cited by examiner

MINIMALLY INVASIVE INTERBODY FUSION

RELATED APPLICATIONS

This application is a U.S. national stage application of PCT Patent Application Serial No. PCT/US2019/015386, filed Jan. 28, 2019, which claims the benefit of and priority of U.S. Provisional Patent Application Ser. No. 62/623,025, filed Jan. 29, 2018, and U.S. Provisional Patent Application Ser. No. 62/718,570, filed Aug. 14, 2018, the contents of all of which are incorporated by reference herein.

DESCRIPTION

Technical Field

The present disclosure generally relates to apparatus and methods employed in minimally invasive surgical procedures and more particularly to various aspects of apparatus and methods for separating and/or supporting tissue layers, especially in the disc space of the spine.

Background

A variety of physical conditions involve two tissue surfaces that, for diagnosis or treatment of the condition, need to be separated or distracted or maintained in a separated condition from one another and then supported in a spaced-apart relationship. Such separation or distraction may be to gain exposure to selected tissue structures, to apply a therapeutic pressure to selected tissues, to return or reposition tissue structures to a more normal or original anatomic position and form, to deliver a drug or growth factor, to alter, influence or deter further growth of select tissues or to carry out other diagnostic or therapeutic procedures. Depending on the condition being treated, the tissue surfaces may be opposed or contiguous and may be bone, skin, soft tissue, or a combination thereof.

One location of the body where tissue separation is useful as a corrective treatment is in the spinal column. Developmental irregularities, trauma, tumors, stress and degenerative wear can cause defects in the spinal column for which surgical intervention is necessary. Some of the more common defects of the spinal column include vertebral compression fractures, degeneration or disruption of an intervertebral disc and intervertebral disc herniation. These and other pathologies of the spine are often treated with implants that can restore vertebral column height, immobilize or fuse adjacent vertebral bones, or function to provide flexibility and restore natural movement of the spinal column. Accordingly, different defects in the spinal column require different types of treatment, and the location and anatomy of the spine that requires corrective surgical procedures determines whether an immobilizing implantable device or a flexible implantable device is used for such treatment.

In a typical spinal corrective procedure involving distraction of tissue layers, damaged spinal tissue is removed or relocated prior to distraction. After the damaged tissue has been removed or relocated, adjacent spinal tissue layers, such as adjacent bone structures, are then distracted to separate and restore the proper distance between the adjacent tissue layers. Once the tissue layers have been separated by the proper distance, an immobilizing or flexible device, depending on the desired treatment, is implanted between the tissue layers. In the past, the implantable treatment devices have been relatively large cage-like devices that require invasive surgical techniques, which require relative large incisions into the human spine.

Such invasive surgical techniques often disrupt and disturb tissue surrounding the surgical site to the detriment of the patient, so implantable treatment devices and methods that utilize minimally invasive procedures may be preferable. Minimally invasive methods and devices may be particularly needed in the area of intervertebral or disc treatment. The intervertebral disc is divided into two distinct regions: the nucleus pulposus and the annulus fibrosus. The nucleus lies at the center of the disc and is surrounded and contained by the annulus. The annulus contains collagen fibers that form concentric lamellae that surround the nucleus and insert into the endplates of the adjacent vertebral bodies to form a reinforced structure. Cartilaginous endplates are located at the interface between the disc and the adjacent vertebral bodies.

The intervertebral disc is the largest avascular structure in the body. The cells of the disc receive nutrients and expel waste by diffusion through the adjacent vascularized endplates. The hygroscopic nature of the proteoglycan matrix secreted by cells of the nucleus operates to generate high intra-nuclear pressure. As the water content in the disc increases, the intra-nuclear pressure increases and the nucleus swells to increase the height of the disc. This swelling places the fibers of the annulus in tension. A normal disc has a height of about 10-15 mm.

There are many causes of disruption or degeneration of the intervertebral disc that can be generally categorized as mechanical, genetic, and biochemical. Mechanical damage includes herniation in which a portion of the nucleus pulposus projects through a fissure or tear in the annulus fibrosus. Genetic and biochemical causes can result in changes in the extracellular matrix pattern of the disc and a decrease in biosynthesis of extracellular matrix components by the cells of the disc. Degeneration is a progressive process that usually begins with a decrease in the ability of the extracellular matrix in the central nucleus pulposus to bind water due to reduced proteoglycan content. With a loss of water content, the nucleus becomes desiccated resulting in a decrease in internal disc hydraulic is pressure, and ultimately to a loss of disc height. This loss of disc height can cause the annulus to buckle with non-tensile loading and the annular lamellae to delaminate, resulting in annular fissures. Herniation may then occur as rupture leads to protrusion of the nucleus.

Proper disc height is necessary to ensure proper functionality of the intervertebral disc and spinal column. The disc serves several functions, although its primary function is to facilitate mobility of the spine. In addition, the disc provides for load bearing, load transfer, and shock absorption between vertebral levels. The weight of the person generates a compressive load on the discs, but this load is not uniform during typical bending movements. During forward flexion, the posterior annular fibers are stretched while the anterior fibers are compressed. In addition, a translocation of the nucleus occurs as the center of gravity of the nucleus shifts away from the center and towards the extended side.

Changes in disc height can have both local and global effects. Decreased disc height results in increased pressure in the nucleus, which can lead to a decrease in cell matrix synthesis and an increase in cell necrosis and apoptosis. In addition, increases in intra-discal pressure create an unfavorable environment for fluid transfer into the disc, which can cause a further decrease in disc height.

Decreased disc height also results in significant changes in the global mechanical stability of the spine. With decreasing height of the disc, the facet joints bear increasing loads and may undergo hypertrophy and degeneration, and may even act as a source of pain over time. Decreased stiffness of the spinal column and increased range of motion resulting from loss of disc height can lead to further instability of the spine, as well as back pain.

Radicular pain may result from a decrease in foraminal volume caused by decreased disc height. Specifically, as disc height decreases, the volume of the foraminal canal, through which the spinal nerve roots pass, decreases. This decrease may lead to spinal nerve impingement, with associated radiating pain and dysfunction.

Finally, adjacent segment loading increases as the disc height decreases at a given level. The discs that must bear additional loading are now susceptible to accelerated degeneration and compromise, which may eventually propagate along the destabilized spinal column.

In spite of all of these detriments that accompany decreases in disc height, where the change in disc height is gradual many of the ill effects may be "tolerable" to the spine and patient and may allow time for the spinal system to adapt to the gradual changes. However, the sudden decrease in disc volume caused by the surgical removal of the disc or disc nucleus may increase the local and global problems noted above.

Many disc defects are treated through a surgical procedure, such as a discectomy in which the nucleus pulposus material is removed. During a total discectomy, a substantial amount (and usually all) of the volume of the nucleus pulposus is removed and immediate loss of disc height and volume can result. Even with a partial discectomy, loss of disc height can ensue. Discectomy alone is the most common spinal surgical treatment, frequently used to treat radicular pain resulting from nerve impingement by disc bulge or disc fragments contacting the spinal neural structures.

The discectomy may be followed by an implant procedure in which a prosthesis is introduced into the cavity left in the disc space when the nucleus material is removed. Thus far, the most common prosthesis is a mechanical device or a "cage" that is sized to restore the proper disc height and is configured for fixation between adjacent vertebrae. These mechanical solutions take on a variety of forms, including solid kidney-shaped implants, hollow blocks filled with bone growth material, push-in implants and threaded cylindrical cages.

A challenge in the use of a posterior procedure to install spinal prosthesis devices is that a device large enough to contact the end plates and expand the space between the end plates of the same or adjacent vertebra must be inserted through a limited space. In the case of procedures to increasing intervertebral spacing, the difficulties are further increased by the presence of posterior osteophytes, which may cause "fish mouthing" or concavity of the posterior end plates and result in very limited access to the disc. A further challenge in degenerative disc spaces is the tendency of the disc space to assume a lenticular shape, which requires a relatively larger implant than often is easily introduced without causing trauma to the nerve roots. The size of rigid devices that may safely be introduced into the disc space is thereby limited.

While cages of the prior art have been generally successful in promoting fusion and approximating proper disc height, typically these cages have been inserted from the posterior approach, and are therefore limited in size by the interval between the nerve roots. Further, it is generally difficult to implant from the posterior approach a cage that accounts for the natural lordotic curve of the lumber spine.

It is desirable to reduce potential trauma to the nerve roots and yet still allow restoration or maintenance of disc space height in procedures involving vertebrae fusion devices and disc replacement, containment of the nucleus of the disc, or prevention of herniation of the nucleus of the disc. In general, minimally invasive surgical techniques reduce surgical trauma, blood loss, and pain. However, despite the use of minimally invasive techniques, the implantation of cage devices for treating the spine typically involves nerve root retraction, an inherently high risk procedure. It is therefore desirable to reduce the degree of invasiveness of the surgical procedures required to implant the device, which may also serve to permit reduction in the pain, trauma, and blood loss, as well as the avoidance and/or reduction of the nerve root retraction.

In minimally invasive procedures, to monitor placement, it is useful that implant devices inserted into spinal tissue be detectable using fluoroscopic imaging systems. However if a device is visible using X-ray technology, then the device can interfere with the detection and monitoring of spinal tissues, such as bone growing into the disc space after a vertebral fusion procedure. Additional advances would also be useful in this area.

SUMMARY

There are several aspects of the present subject matter which may be embodied separately or together in the devices, systems, and/or methods described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a tissue distraction device includes at least one elongated member, with a shaping member being removably associated with the at least one elongated member. The at least one elongated member and the shaping member are configured to change from a generally linear configuration to a generally less linear configuration, with the shaping member being configured to automatically move from the generally linear configuration to the generally less linear configuration. Automatic movement of the shaping member from the generally linear configuration to the generally less linear configuration causes movement of the at least one elongated member from the generally linear configuration to the generally less linear configuration.

In another aspect, a tissue distraction device includes at least one elongated member comprised of an elongated internal core member and a plurality of veneer members at least partially surrounding the internal core member and spaced along the length of the internal core member. The internal core member is sufficiently flexible to change between a generally linear configuration and a generally less linear configuration, while the plurality of veneer members are substantially formed of a generally rigid material.

In yet another aspect, a tissue distraction system includes a tissue distraction device and an injection aid. The tissue distraction device is configured to be positioned between tissue layers, includes an elongated guide member, and defines a window into its interior. The injection aid includes a follower member and a funnel member, with the funnel member defining a lumen and extending between a proximal end configured to accommodate at least a portion of an injector device and a distal end. The follower member is associable with the guide member to align the distal end of the funnel member with the window of the tissue distraction device and to allow movement of the injection aid along at least a portion of the length of the guide member to position the distal end of the funnel member adjacent to the window, at least partially inside of the window, or in the interior of the tissue distraction device via the window for introduction of a filler material into the interior of the tissue distraction device.

In another aspect, a tissue distraction system includes a tissue distraction device configured to be positioned between tissue layers. The system also includes a deployment cannula extending between proximal and distal ends and configured for introduction of the tissue distraction device between the tissue layers. The tissue distraction device has a dimensional aspect in a direction extending between the tissue layers, with the dimensional aspect of at least a portion of the tissue distraction device being configured to increase while the tissue distraction device is at least partially positioned at the distal end of the deployment cannula. At least a portion of the distal end of the deployment cannula is configured to deform to accommodate the increase of the dimensional aspect of the tissue distraction device while the tissue distraction device is at least partially positioned at the distal end of the deployment cannula.

In yet another aspect, a method is provided for manufacturing a tissue distraction device. The method includes forming a lower portion of at least one veneer member. An intermediate layer is formed onto the lower portion so as to define a cavity. At least a portion of an elongated internal core member is inserted into the cavity. An upper portion is formed onto the intermediate portion so as to enclose the internal core member within the cavity. The veneer member is generally rigid, while the internal core member is configured to change from a generally linear configuration to a generally less linear configuration.

In another aspect, a method is provided for manufacturing a tissue distraction device. The method includes forming a single body piece defining a plurality of generally rigid body elements each connected to an adjacent body element by at least one frangible bridge. The single body piece is associated to a generally flexible internal core member, which is moved from a generally linear configuration to a generally less linear configuration to break the bridges and separate each body element from the adjacent body element.

DETAILED DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

The devices and methods of the present disclosure provide multiple features of distraction devices, distraction device support structures, and deployment systems that can be used to actively separate tissue layers by engaging them and forcing them apart, or to support the separation of tissue layers separated by the distraction device itself or by other devices or processes or a combination of these.

As used herein, the phrases "distraction device" and "support structure" are intended to have a general meaning and are not limited to devices that only actively separate tissue layers, only support tissue layers or only both actively separate and support tissue layers. For example, a distraction device or support structure in general can be used to actively separate layers of tissue and then be removed after such separation, or a distraction device or support structure could be used to support layers of tissue that have been previously separated by a different device. Alternatively, a distraction device or support structure can be used to actively separate the layers of tissue and remain in place to support the layers of tissue in order to maintain such separation. Unless more specifically set forth in the claims, as used herein, the phrases "distraction device" and "support structure" encompass any and all of these. In addition, it should be noted that the references to "first" and "second" members or devices are for convenience in the written description. They may be combined to provide a single distraction assembly or structure of selected distraction height, and the assembly is not limited to any particular number of "devices" or "members." In keeping with the broader aspects of the present disclosure, the specific number of "devices" or "members" can be varied according to the intended usage or design considerations.

It should also be understood that various embodiments of the devices, systems, and methods of the present disclosure are illustrated for purposes of explanation in vertebral fusion procedures and/or replacement of removed discs. However, in its broader aspects, the various features of the present disclosure are not limited to these particular applications and may be used in connection with other tissue layers, such as soft tissue layers, although it has particular utility and benefit in treatment of vertebral conditions within intervertebral discs or disc spaces.

Figure 1:
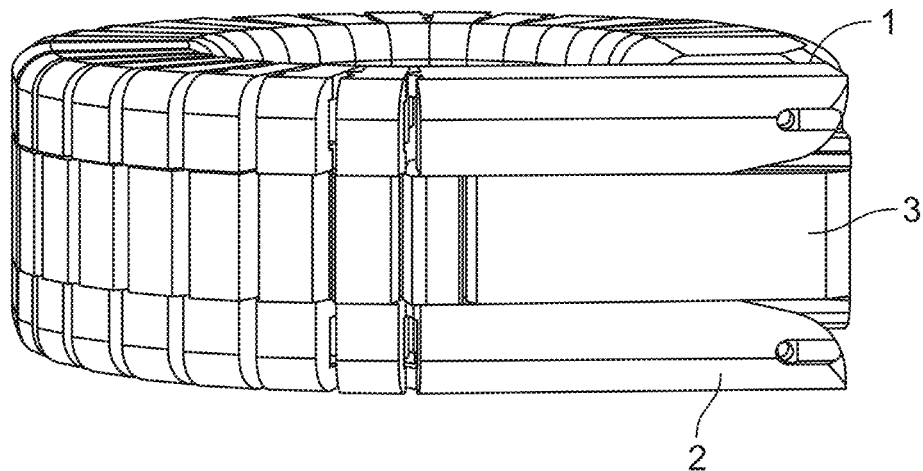
FIG. 1 is a side elevational view of a distraction device according to an aspect of the present disclosure, in a generally less linear configuration.
Figure 2:
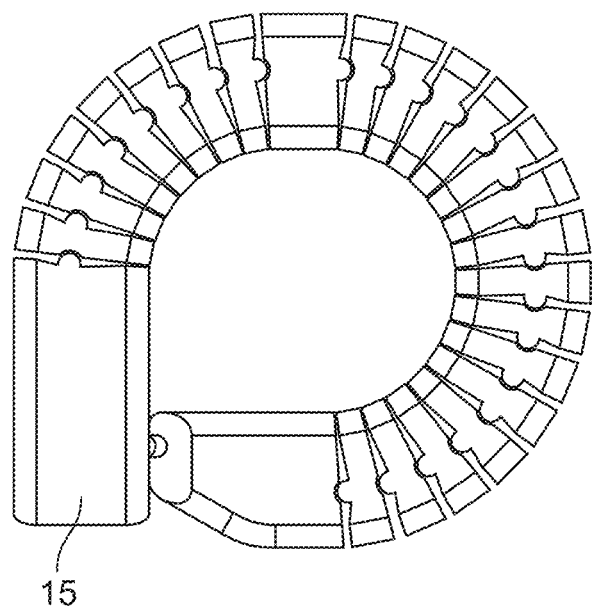
FIG. 2 is a top plan view of the distraction device of FIG. 1.

One embodiment of a distraction device or support structure or implant is shown in FIGS. 1 and 2. The distraction device shown in FIGS. 1 and 2 is comprised of a first or upper elongated member 1, a second or lower elongated member 2, and an augmenting elongated member 3. The augmenting elongated member 3 cooperatively interacts with the first and second elongated members 1 and 2 to increase a dimensional aspect of the distraction device or support structure. The distraction device is preferably comprised of elongated members made of biocompatible materials (including metals and polymers) that are suitable for long-term implantation into human tissue where treatment is needed. The biocompatible materials may, for example, be calcium phosphate, tricalcium phosphate, hydroxyapatite, polyetheretherketone (PEEK), nylon, titanium, Nitinol (NiTi) or any other suitable biocompatible material. Suitable biocompatible material may also include PEEK with carbon fibers, polyethylenes of low, medium, and/or high densities, as well as nylons and blends of materials that contain nylons. It is also within the scope of the present disclosure for the elongated members to be at least partially comprised of one or more bioabsorbable materials, such as polyglycolic acid (PGA) or poly-L lactic acid (PLLA), for example. To the extent not contradicted by the present disclosure, elongated members according to the present disclosure may be manufactured, configured, and function generally according to the disclosures of U.S. Pat. Nos. 8,454,617 and 9,480,574, both of which are hereby incorporated herein by reference.

Figure 3:
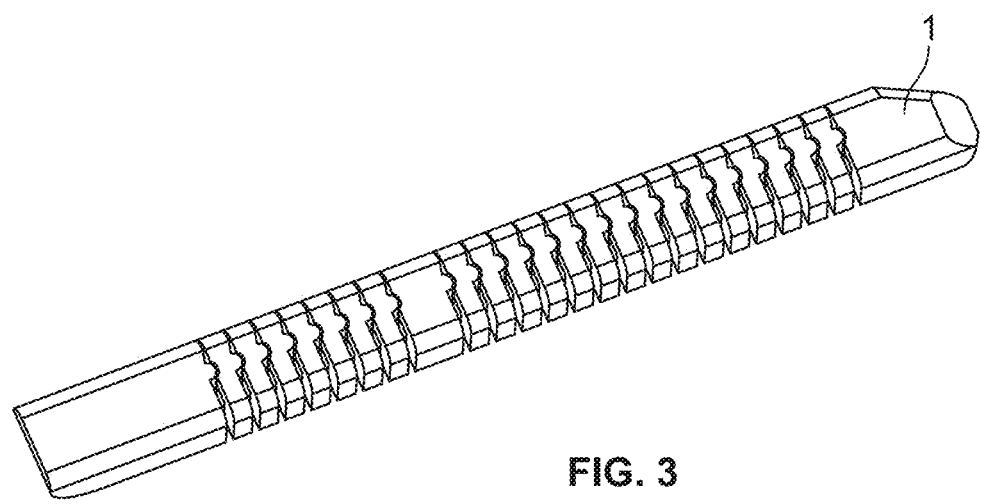
FIGS. 3 and 4 are top perspective views of an upper elongated member of the distraction device of FIG. 1 in a generally linear configuration, with FIG. 4 showing interior elements of the upper elongated member.
Figure 4:
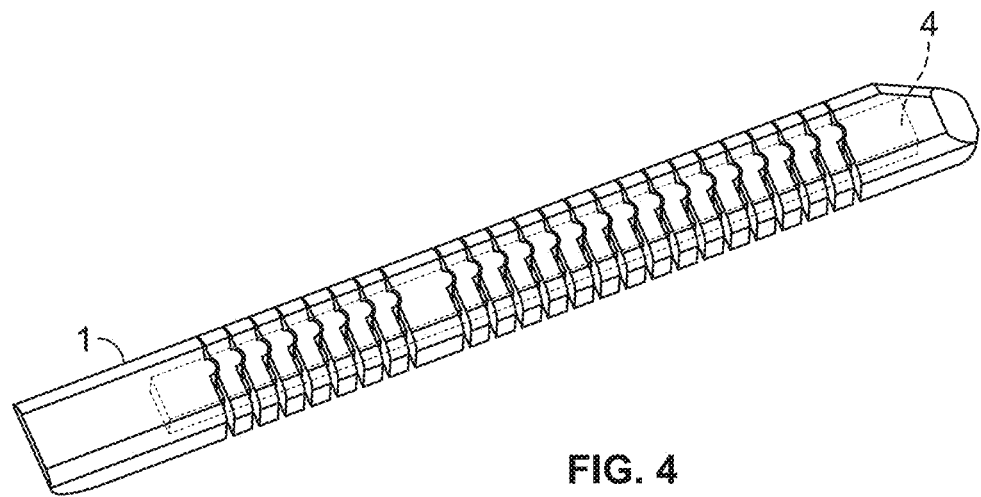
Figure 5:
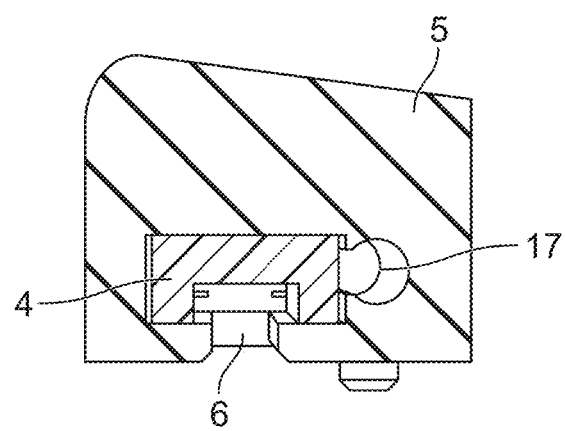
FIG. 5 is a cross-sectional view of the upper elongated member of FIGS. 3 and 4.

According to one aspect of the present disclosure, the first and/or second elongated members 1 and 2 are provided with a hybrid or composite structure, rather than a unitary structure. For example, FIGS. 3-5 show the configuration of an exemplary embodiment of the first elongated member 1, with the understanding that the second elongated member 2 may be a mirror image of the first elongated member 1 or may be differently configured. In the illustrated embodiment, the first elongated member 1 is formed of an elongated internal core member 4 and a plurality of outer skin or veneer elements or members 5, which at least partially surround the internal core member 4 (as best shown in FIG. 5) and which are spaced along the length of the internal core member 4.

Figure 9:
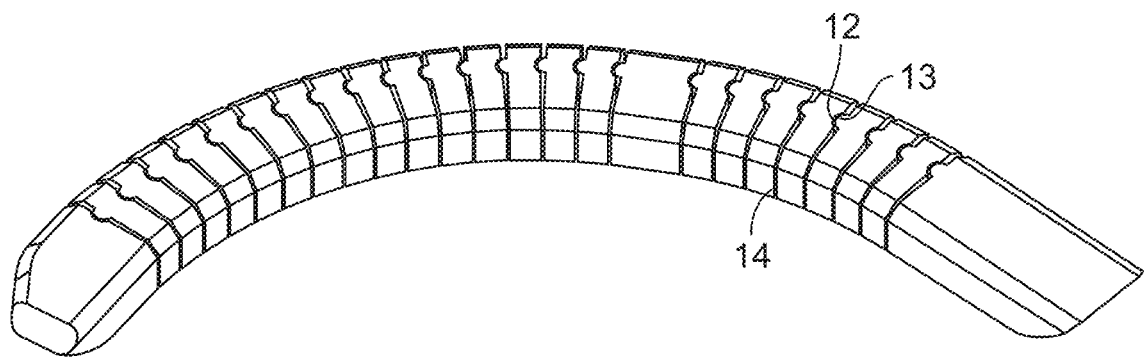
FIG. 9 is a bottom plan view of a lower elongated member of the distraction device of FIG. 1, in a generally less linear configuration.
Figure 10:
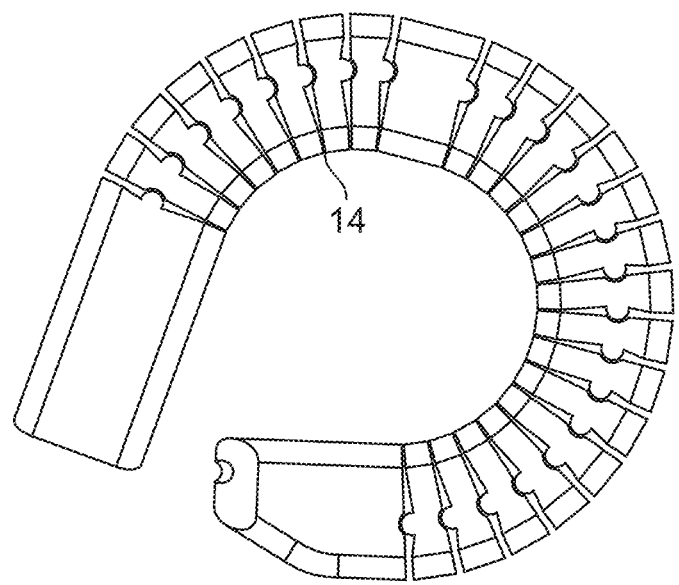
FIG. 10 is a top plan view of the lower elongated member of FIG. 9, in another generally less linear configuration.

Preferably, the elongated members which form the distraction device are configured to change (e.g., by flexing or bending) between a generally linear configuration for insertion into tissue or between tissue layers (FIGS. 3 and 4) and generally less linear configurations when deployed between tissue layers (FIGS. 1 and 2) to define the tissue distraction device. While FIGS. 1 and 2 show the elongated members in a generally annular configuration, it should be understood that in changing from the generally linear configuration to the generally annular or closed loop configuration of FIGS. 1 and 2, the elongated members pass through intermediate, generally less linear configurations (see FIGS. 9 and 10, for example), which are more arcuate and less linear than the insertion configuration of FIGS. 3 and 4, but less annular than the fully deployed configuration of FIGS. 1 and 2. As used herein, the term "annular" is not limited to substantially circular distraction devices and elongated members, but may include other closed shapes, such as ovals and rectangles, or substantially closed versions of such shapes.

To allow a hybrid elongated member (of the type shown in FIGS. 3 and 4) to so change in configuration, the internal core member 4 is preferably formed of a flexible material, such as PEEK or another polymer, with the internal core member 4 being manufactured using any of a number of suitable techniques, including machining or milling techniques. Milling can include cutting an internal core member 4 (or the body of a non-hybrid elongated member, such as the augmenting elongated member 3) from solid blocks or rods of PEEK or other suitable material. An internal core member 4 (or body of a non-hybrid elongated member) may also be manufactured using molding or extrusion techniques. In addition, the internal core members 4 (or bodies or non-hybrid elongated members) of the present disclosure may be manufactured with electrical discharge machining processes and by rapid prototyping methods including fused deposition modeling (FDI) and stereo lithography (SLA) techniques.

In contrast to the internal core member 4, the outer veneer members 5 may be formed of a generally rigid material, such as a metallic material. In one embodiment, the outer veneer members 5 are formed of a titanium material, which has excellent biocompatibility with human tissue, particularly when at least a portion of an outer surface of the outer veneer members 5 (preferably a portion oriented to engage a tissue layer) is formed so as to have a rough, porous surface for improved biological fixation. Regardless of the material composition and particular configuration of the outer veneer members 5, they may be formed by any of a number of suitable approaches, including a 3D printing approach.

Figure 5A:
FIGS. 5A-5D illustrate an exemplary method for manufacturing the upper elongated member of FIGS. 3 and 4.
Figure 5B:
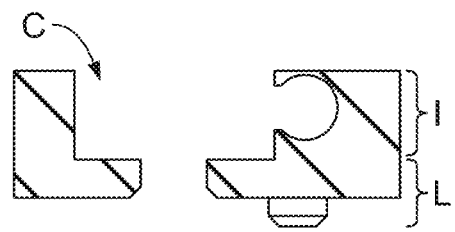
Figure 5C:
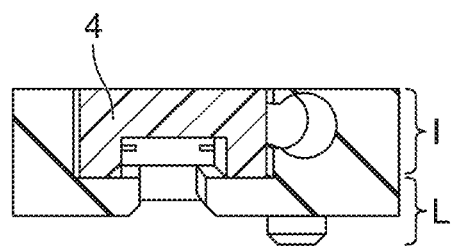
Figure 5D:
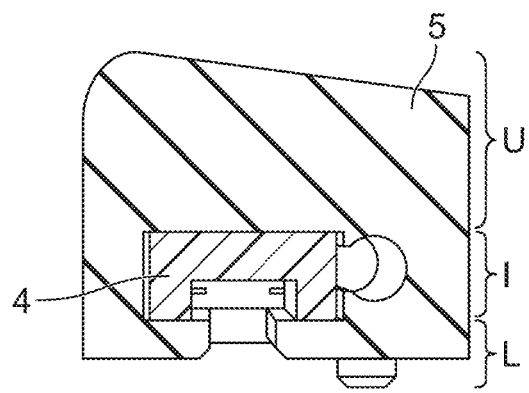

According to an exemplary approach to associating the internal core member 4 to the veneer members 5, one or more of the veneer members 5 may be partially formed, followed by the internal core member 4 being inserted into the partially formed veneer member 5. With the internal core member 4 so positioned, the remainder of the veneer member 5 may be formed around the internal core member 4 so as to enclose or entrap the internal core member 4 within a cavity of the veneer member 5. Such an approach is shown in FIGS. 5A-5D. In FIG. 5A, a lower portion "L" of the veneer member 5 is formed. An intermediate portion "I" of the veneer member 5 may then be formed onto the lower portion "L", as in FIG. 5B. The intermediate portion "I" is formed so as to define a cavity "C". With the veneer member 5 in the partially formed condition of FIG. 5B, a corresponding portion of the internal core member 4 is inserted into the cavity "C", as shown in FIG. 5C. Finally, when the internal core member 4 has been properly positioned within the cavity "C", an upper portion "U" of the veneer member 5 is formed onto the intermediate portion "I", thus completing the formation of the veneer member 5, as in FIG. 5D. Following formation of the veneer member 5, it may be subjected to additional processing before being ready for use.

The various portions of the veneer member 5 may be sequentially formed using any suitable approach, including three-dimensional ("3D") printing. A 3D-printed object is formed by sequentially forming a plurality of thin layers of material, with each successive layer being positioned at least partially above and onto the immediately preceding layer. Thus, if the veneer member 5 of FIGS. 5A-5D is formed via 3D printing, a first lower layer is applied to a platform or printing bed. A second lower layer is applied onto the first lower layer, followed by subsequent lower layers being applied onto each other until the lower portion "L" of FIG. 5A has been formed. Next, a first intermediate layer is applied onto the uppermost lower layer (i.e., onto the lower portion "L"), followed by subsequent intermediate layers being applied onto each other until the intermediate portion "I" of FIG. 5B has been formed. Then, after the internal core member 4 has been inserted into the cavity "C" defined by the intermediate portion "I", a first upper layer is applied onto the uppermost intermediate layer (i.e., onto the intermediate portion "I"), followed by subsequent upper layers being applied onto each other until the upper portion "U" (and, hence, the veneer member 5) has been completely formed.

The individual layers may be formed by any suitable approach. For example, if the veneer member 5 is to be formed of a metallic material, a thin layer of metal powder may be applied to a printing bed and sintered using a laser system. Another layer of metal powder is then applied onto the first layer, with the second layer being sintered using the laser system. This process is repeated until enough layers of metal powder have been applied and sintered to form the various portions of the veneer member 5, with the process being suspended between formation of the intermediate portion "I" and the upper portion "U" to allow for insertion of the internal core member 4. Other approaches to forming the various layers are described in U.S. Pat. No. 9,937,580 (which describes a method of using a hot-wire, with a laser precisely melting metal at a desired location) and U.S. Pat. No. 10,029,406 (which describes a method in which feedstock of material is fed onto a fabrication platform and melted by a high-energy source to form a molten droplet or particle at the point of contact), both of which are hereby incorporated herein by reference. It should be understood that these approaches are merely exemplary, and that other approaches may also be employed without departing from the scope of the present disclosure.

Figure 7:
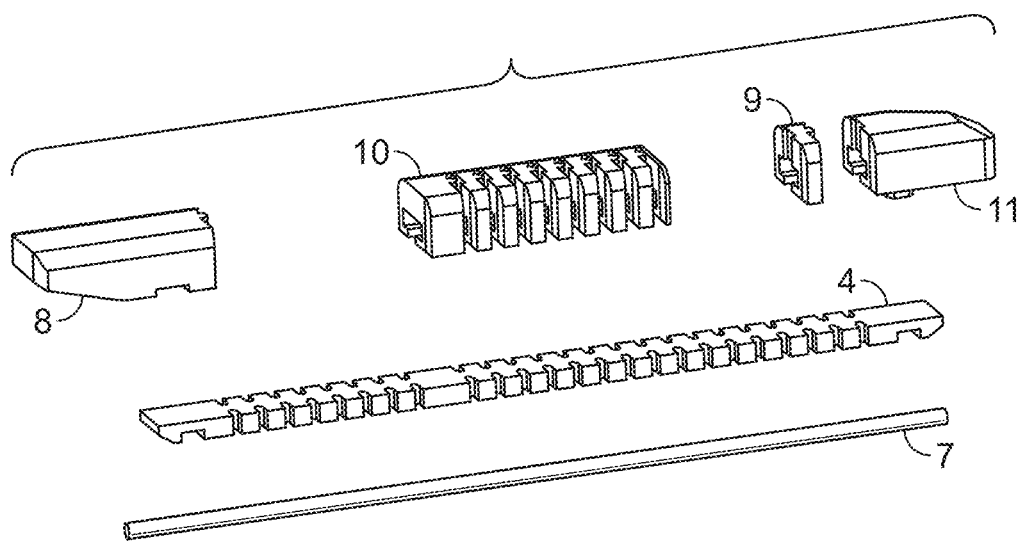
FIG. 7 is an exploded view of the upper elongated member of FIGS. 6A and 6B.

Regardless of how exactly the individual veneer members 5 are formed, it should be understood that the outer veneer members 5 may be differently configured from each other, rather than being identical. For example, FIG. 7 shows examples of differently configured outer veneer members 5 that may be incorporated into a single elongated member. In the embodiment of FIG. 7, the outer veneer members 5 are shown as being provided in four different configurations: the single proximal end piece 8; a plurality of common body elements or plates 9, which are short or plate-like and allow for stacking; the single enlarged body element 10, which is of similar design to the other body elements 9, but longer to indicate the optimal anterior position of the distraction device once in its deployed configuration; and the single distal end piece or nose piece 11. The proximal and distal end pieces 8 and 11 may be mounted and fixed to the internal core member 4 using any suitable approach, which may include the method illustrated in FIGS. 5A-5D, adhesion, pressed-fitting, swaging, welding, or pinning. So affixing the end pieces 8 and 11 to the internal core member 4 effectively traps the common and enlarged body elements 9 and 10 between the end pieces 8 and 11, without the body elements 9 and 10 having to be secured to the internal core member 4, which allows the body elements 9 and 10 to move or articulate with respect to the internal core member 4, as will be described in greater detail. By such a configuration, the internal core member 4 and outer veneer members 5 combine to form a continuous, semi-rigid hybrid elongated member.

Figure 6A:
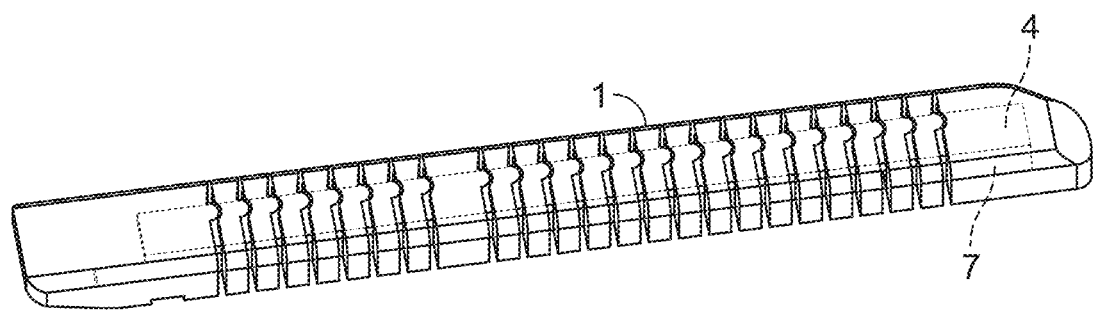
FIGS. 6A and 6B are top perspective views of an alternative embodiment of an upper elongated member in a generally linear configuration, with FIG. 6A showing interior elements of the upper elongated member.
Figure 6B:
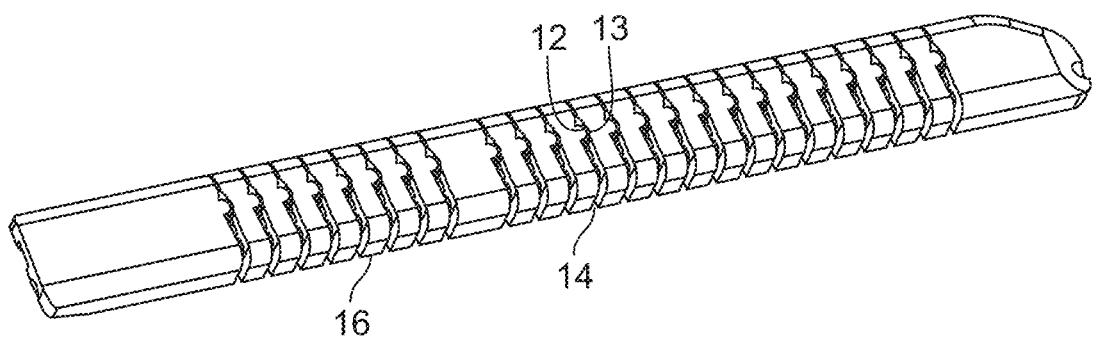

As noted above, the common body elements 9 and the enlarged body element 10 may articulate with respect to the internal core member 4 to which they are mounted. In one embodiment, which is best seen in FIG. 6B, each of the body elements 9 and 10 may be formed with a dimple 12 and receptacle 13 on opposing end faces, with the dimple 12 of one body element 9, 10 being at least partially received by the receptacle 13 of an adjacent body element 9, 10. Such a configuration allows for engagement and rotation as the hybrid elongated member is flexed and moved from a generally linear configuration to a generally less linear configuration. More particularly, the dimple/receptacle pairs function like a swivel, with there being a gap 14 between inner edges 16 of adjacent body elements 9 and 10 being sufficiently sized so as to not interfere with the articulation of the body elements 9 and 10 required for the hybrid elongated member to move to a generally annular or closed loop configuration, as in FIGS. 1 and 2. Indeed, in one embodiment, the body elements 9 and 10 are configured such that there remains a gap 14 between the inner edges 16 of adjacent body elements 9 and 10 when a closed loop is formed by the distal end piece 11 coming into contact with a side surface of the proximal end piece 8, as shown in the circle detail 15 of FIG. 2. In an alternative embodiment, the body elements 9 and 10 may be configured such that the inner edges 16 of adjacent body elements 9 and 10 do come into contact with each other upon the hybrid elongated member moving into its final deployed configuration, which limits the amount of flexion that can be accomplished.

The distal ends of the first and second elongated members 1 and 2 (whether provided with a hybrid or non-hybrid configuration) can have chamfer or incline or wedge features to ease the passage of the elongated member through tissue, such as bone or vertebral disc material. For example, FIG. 2 shows a chamfer or incline feature visible on the upper surface of the distal end of the first elongated member 1. It should be understood that the lower surface of the distal end of the second elongated member 2 may include a similar chamfer feature.

A non-hybrid elongated member of the distraction device may also include features that add flexibility to the elongated member to assist in bending or changing the configuration of the elongated member from a generally linear configuration to a less linear configuration and vice versa. For example, a non-hybrid elongated member may include lateral teeth and intermediate slots or indents (similar in structure to the inner edges 16 and gaps 14 of the body elements 9 and 10 of a hybrid elongated member) that aid in relieving stress and add flexibility to the elongated member. When the elongated member is deployed in tissue, the slots may also provide gaps for the introduction of bone filler or bone graft materials, cements, or pharmaceutical compounds to the tissues.

Figure 11:
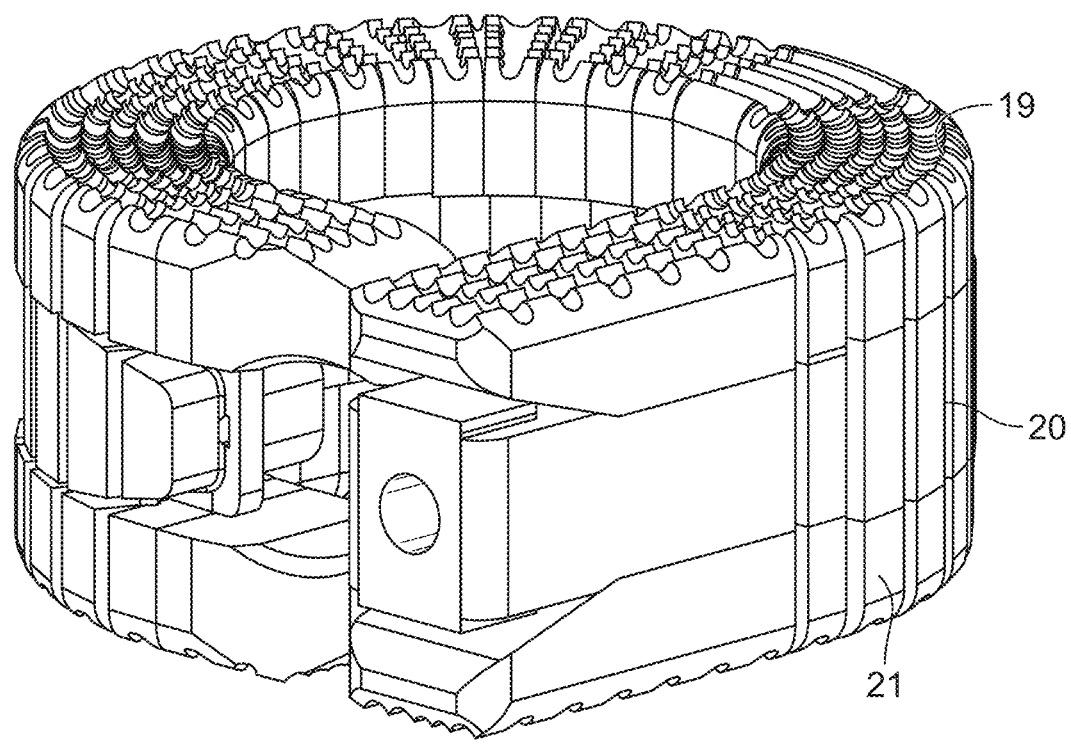
FIGS. 11 and 12A are end perspective views of the distraction device of FIG. 1, with FIG. 12A showing interior elements of the distraction device.
Figure 20:
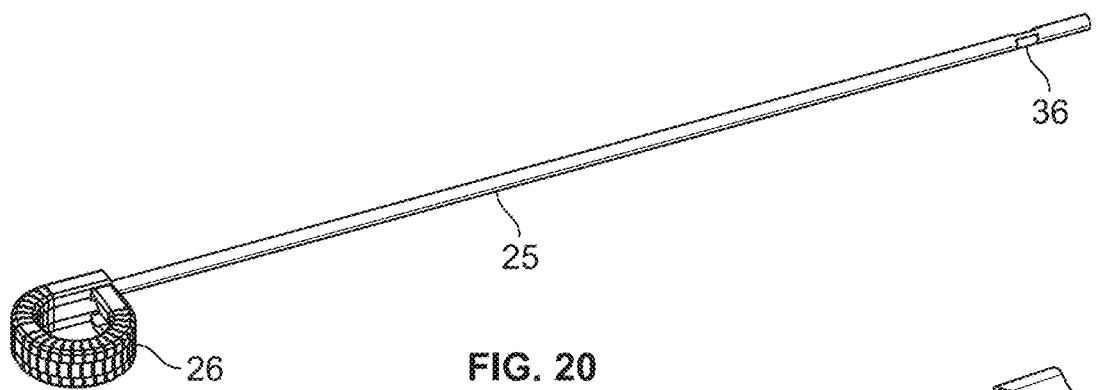
FIG. 20 is bottom perspective view of the distraction device of FIG. 1, with an associated guide member.
Figure 21:
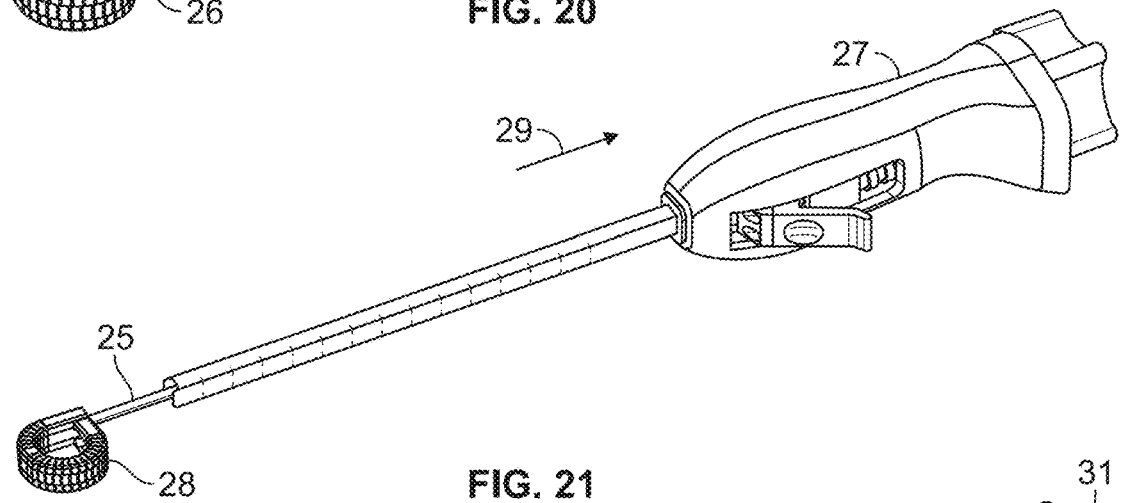
FIG. 21 is a bottom perspective view of the distraction device of FIG. 20, showing a deployment device being moved away from the distraction device, along the guide member.

Other features may also be added to enhance the functionality of the elongated members, including grooves, slots, channels, and pockets and teeth or other extensions of various shapes. For example, the proximal end of the augmenting elongated member 3 may be provided with a cavity (FIG. 11) configured to receive the distal portion of a removable, elongated guide member 25 (FIG. 20). The structure and function of the guide member 25 will be described in greater detail herein.

Figure 27:
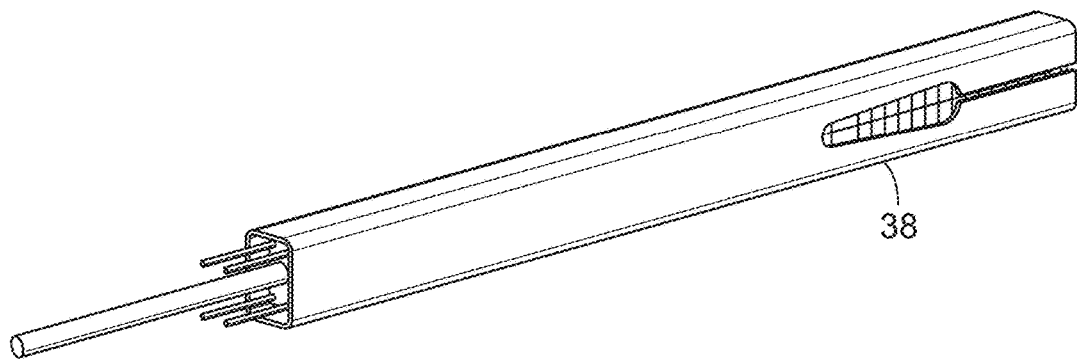
FIG. 27 is a perspective view of a cannula of the deployment device of FIG. 26, with components of a distraction device positioned therein.

The first and second elongated members 1 and 2 may be provided with formations that assist in maintaining the position of the first and second elongated members 1 and 2 while the augmenting elongated member 3 is inserted therebetween. As shown in FIG. 27, an anchoring or tethering system or wires can be used to hold the first and second elongated members 1 and 2 in place while the augmenting elongated member 3 is inserted between the first and second elongated members 1 and 2. The illustrated tethering system includes a pair of anchor wires or cables or filaments, each of which attaches to the proximal end of one of the first and second elongated members 1 and 2. Each anchor wire may include an enlarged end (e.g., a generally spherical or ball-shaped end piece) that is at least partially received within a cavity defined within the proximal end of the associated elongated member (FIG. 1). Such an anchoring system is described in greater detail in U.S. Pat. No. 9,480,574.

The first and second elongated members 1 and 2 may also be provided with a slot 6 (FIG. 5) extending along all or a portion of their lengths to receive a complementary raised rib or formation of the augmenting elongated member 3 to prevent separation of the elongated members. In one embodiment, the slot 6 has a relatively narrow necked-down portion and a wider portion to receive a generally T-shaped raised rib of the augmenting elongated member 3, as described in greater detail in U.S. Pat. No. 9,480,574. In the case of a hybrid configuration, the relatively narrow necked-down portion of the slot 6 may be defined by the outer veneer members 5, while a wider portion of the slot 6 may be defined by the internal core member 4, as in the embodiment of FIG. 5.

One or more of the elongated members may also be provided with a formation that accommodates a shaping member. For example, FIG. 5 shows an outer veneer member 5 having a through hole or aperture 17 positioned adjacent to the cavity that accommodates the internal core member 4. Although not provided in the embodiment of FIGS. 3-5, a hybrid elongated member may include a shaping member 7 (FIGS. 6A-7) received in the aligned holes 17 of the outer veneer members 5, as in the embodiment of FIGS. 6A and 6B. A non-hybrid elongated member, such as the augmenting elongated member of FIGS. 12A and 12B may include a similarly configured bore or channel configured to receive a shaping member 22. If provided, the shaping members 7 and 22 are preferably fixed in place within the associated elongated member according to any of a number of suitable approaches to prevent the shaping member 7, 22 from backing out or otherwise becoming free of the associated elongated member.

Figure 8:
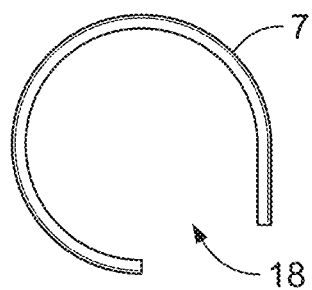
FIG. 8 is a top plan view of a shaping member of the upper elongated member of FIGS. 6A-7, in a generally less linear configuration.

The shaping member 7, 22 may be configured as an elongated rod formed of a shape memory material, such as nitinol. The shaping member 7, 22 provides the force required to deflect the associated elongated member from its generally linear configuration to a generally less linear configuration. FIG. 8 shows a shaping member 7 in a free, unconstrained state, which corresponds to the generally annular or closed loop configuration that the elongated members may assume in their final deployed configurations of FIGS. 1-2 and 11. The configuration of FIG. 8 may be imparted to the shaping member 7, 22 according to a heat-treating process of the type that is well-known to those experienced in working with shape memory materials.

Figure 12A:
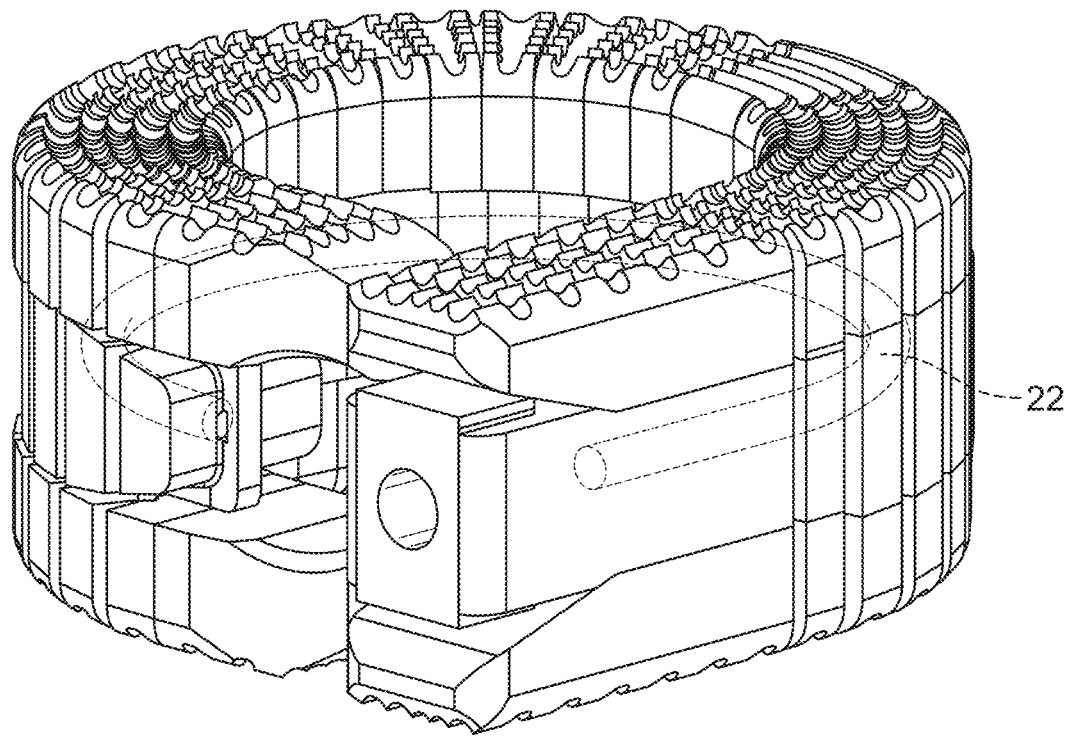
Figure 12B:
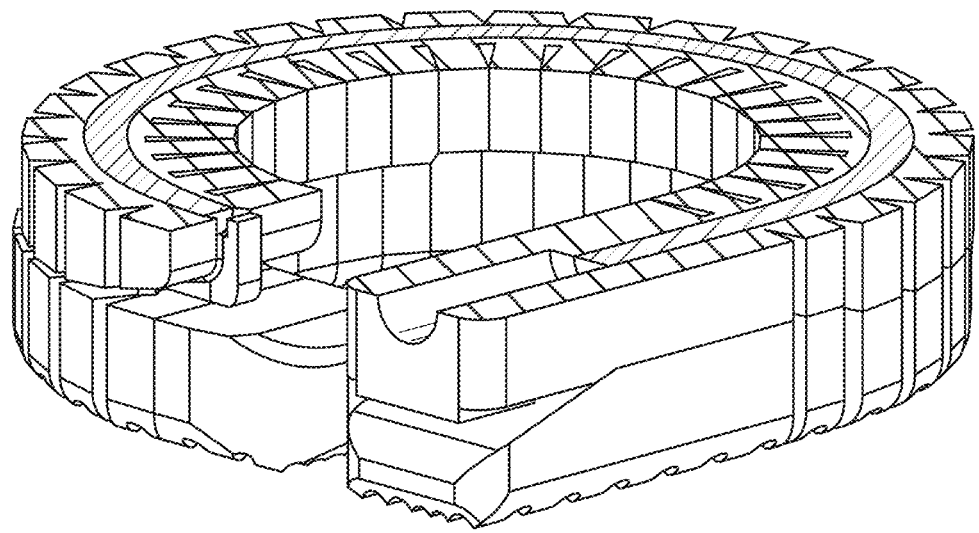
FIG. 12B is a cross-sectional view of the distraction device of FIGS. 11 and 12A.
Figure 13:
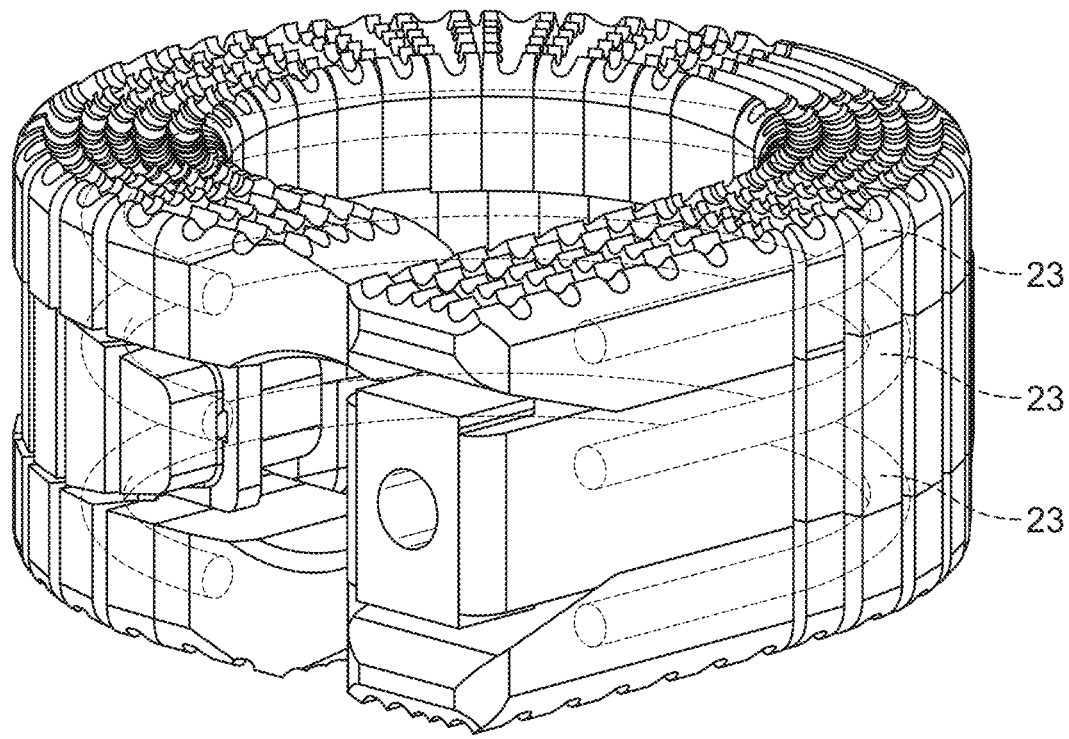
FIG. 13 is an end perspective view of an alternative embodiment of the distraction device of FIGS. 11 and 12A, showing interior elements of the distraction device.
Figure 14:
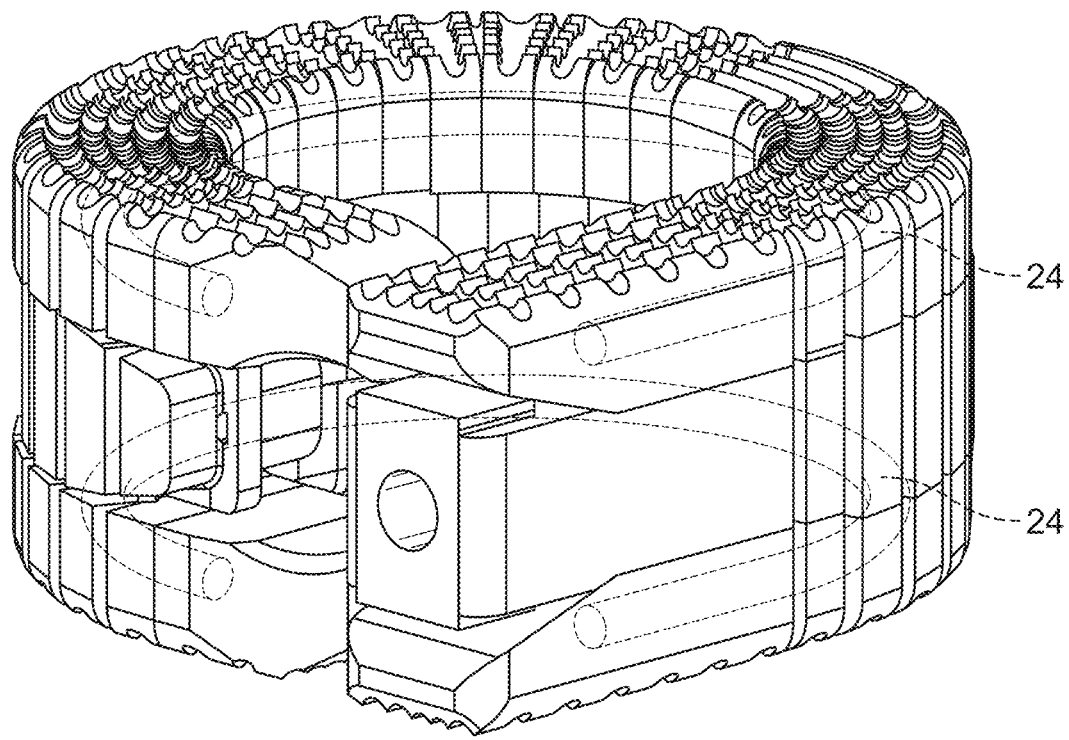
FIG. 14 is an end perspective view of another alternative embodiment of the distraction device of FIGS. 11 and 12A, showing interior elements of the distraction device.

One or more of the elongated members may be provided with a shaping member. For example, FIGS. 12A and 12B show an embodiment in which only the augmenting elongated member 3 includes an associated shaping member 22. FIG. 13 shows an embodiment in which each of the elongated members includes an associated shaping member 23, while FIG. 14 shows an embodiment in which only the first and second elongated members 1 and 2 are provided with associated shaping members 24. It should be understood that these illustrated embodiments are merely exemplary and that, in other embodiments, only one of the first and second elongated members 1 and 2 may be provided with an associated shaping member (with the augmenting elongated member 3 and the other elongated member omitting a shaping member) or one of the first and second elongated members 1 and 2 and the augmenting elongated member 3 may be provided with associated shaping members, while the other one of the first and second elongated member omits a shaping member. Further, it should be understood that other aspects of the present disclosure may be embodied in or employed in combination with a distraction device omitting a shaping member.

The number and position of the shaping member or members, if provided, affects the operation of the resulting distraction device. For example, providing a shaping member 22 in only the augmenting elongated member 3 (as in FIG. 12) could make it simpler to incorporate an anchoring system into the first and second elongated members 1 and 2, as noted above. On the other hand, incorporating a shaping member 13 into each of the elongated members (as in FIG.

13) would provide a greater closing/holding force in a generally annular or closed loop configuration compared to an embodiment having fewer than three shaping members. Incorporating shaping members 24 into only the first and second elongated members 1 and 2 (as in FIG. 14) may better allow for removal and repositioning of the augmenting elongated member 3, in the event that a revision needs to occur during deployment of the distraction device.

In an alternative embodiment, the first and/or second elongated member 1 and 2 may be provided with an elongated shaping member that extends proximally out of the proximal end of the elongated member, rather than being fully embedded within the elongated member. By such a configuration only the distal portion of the shaping member (i.e., the portion positioned within the associated elongated member) is configured to automatically move from the generally linear configuration to a generally less linear configuration, with the remainder of the shaping member (i.e., the portion extending proximally out of the associated elongated member) being configured to remain in a generally linear configuration. The distal portion of the shaping member would be allowed to automatically move the associated elongated member from the generally linear configuration to a generally less linear configuration (which may be its final generally linear configuration), followed by the shaping member being withdrawn from the associated elongated member upon the distraction device being fully deployed between the tissue layers. In such an embodiment, the augmenting elongated member 3 may be provided with a fully embedded shaping member 7, as described above, which remains in the augmenting elongated member 3 following implantation of the distraction device.

In another alternative embodiment, rather than a hybrid elongated member including both an internal core member 4 and a shaping member 7, the internal core member 4 may be at least partially formed of a shape memory material to provide the functionality of the shaping member 7. It may be advantageous for such an internal core member 4 to be partially formed of a PEEK material or other radiopaque material to allow for detection and visualization of the internal core member 4 during implantation. For example, the internal core member 4 may comprise a shape memory material coated with a PEEK material or other radiopaque material to combine the functionality of the previously described internal core member 4 and shaping member 7. Additionally, if the internal core member 4 is at least partially formed of a shape memory material, it may be advantageous for it to be formed with slots or other formations for enhanced flexibility, as the internal core member 4 typically has a greater cross-sectional area than the shaping member 7, which may require such flexibility-enhancing features to allow the internal core member 4 to move from the generally linear configuration to a final generally less linear configuration.

Figure 15:
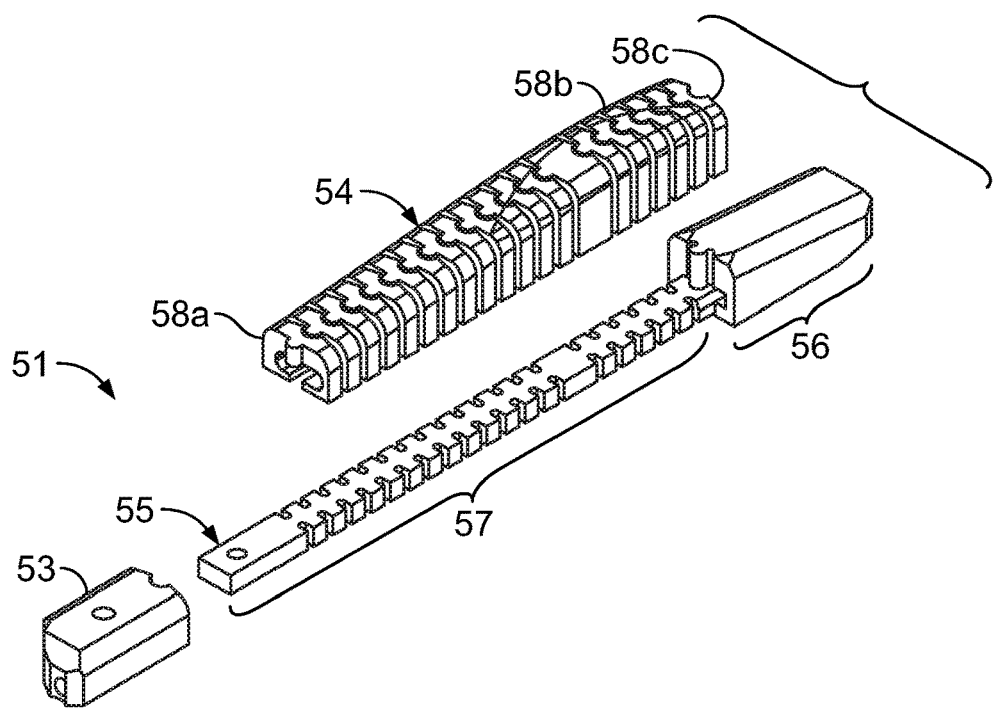
FIG. 15 is an exploded view of an upper elongated member of another alternative embodiment of a distraction device according to an aspect of the present disclosure.

FIGS. 15-19 illustrate yet another embodiment of a tissue distraction device 50 according to the present disclosure, which may be particularly configured for lordotic correction. The embodiment of FIGS. 15-19 is similar to other embodiments described herein, but includes a number of differences, which may be incorporated into the other embodiments described herein. For example, FIG. 15 shows the components of an upper elongated member 51 of the tissue distraction device 50 that may be compared to the components of the upper elongated member of FIG. 7. FIG. 7 shows an upper elongated member comprised of a proximal end piece 8, a plurality of common body elements or plates 9, a single enlarged body element 10, a distal end piece or nose piece 11, an internal core member 4, and a shaping member 7. In the embodiment of FIGS. 15-19, an upper elongated member 51 (and/or a lower elongated member 52) is comprised of a distal end piece 53 (which may be configured similarly to the distal end piece 11 of FIG. 7), a single body piece 54, and a modified proximal end piece 55. While FIG. 15 does not illustrate a shaping member, it should be understood that a shaping member may be included without departing from the scope of the present disclosure.

The modified proximal end piece 55 of FIG. 15 may be understood as a combination of the proximal end piece 8 and the internal core member 4 of FIG. 7, with a proximal portion 56 thereof configured similarly to the proximal end piece 8 of FIG. 7 and a distal portion 57 thereof configured similarly to a portion of the internal core member 4 of FIG. 7. By providing a single piece 55 in place of the two pieces of FIG. 7, assembly of the elongated member 51 may be simplified, with the distal portion 57 of the modified proximal end piece 55 (which may be referred to herein as the internal core member) providing a platform onto which the body piece 54 and then the distal end piece 53 may be slid in a proximal direction. The distal end piece 53 may be secured to the internal core member 57 by any suitable approach (e.g., being pinned, screwed, mechanically fastened, or adhered) to trap the body piece 54 between the distal end piece 53 and the proximal portion 56 of the modified proximal end piece 55. While FIG. 15 shows the internal core member 57 monolithically formed with the proximal portion 56, it should be understood that the internal core member 57 may instead be incorporated into the distal end piece 53.

As the internal core member 57 is preferably flexible (to allow for a change in the configuration of the elongated member 51 during implantation), the modified proximal end piece 55 is preferably formed of a flexible material, such as PEEK or another polymer, with the modified proximal end piece 55 being manufactured using any of a number of suitable techniques, including machining or milling techniques. Thus, rather than the proximal portion 56 being formed of a generally rigid material (as is the case with the proximal end piece 8 of FIG. 7), the proximal portion 56 is instead formed of a more flexible material. However, while the entire modified proximal end piece 55 may be formed of the same generally flexible material, it should be understood that the proximal portion 56 will tend to be less deformable than the internal core member 57 due to it having a larger cross section.

Turning now to the modified body piece 54, it comprises a plurality of individual outer veneer members or body elements 58a-58c (collectively referred to as 58) corresponding generally to the common body elements or plates 9 and enlarged body element 10 of FIG. 7. Rather than being separately formed, at least two of the individual body elements 58 of the modified body piece 54 are formed (e.g., by 3D printing or any other suitable approach) as a single piece, rather than all of the body elements 58 being separately formed. In the illustrated embodiment, all of the body elements 58 are formed as a single piece, but it should be understood that one or more of the body elements 58 may be separately provided. Each constituent body element 58 of the modified body piece 54 may be connected to the adjacent body element 58 by one or more frangible bridges 59 (FIGS. 16 and 17) that are configured to be broken to separate the previously connected body elements 58. In such an embodiment, the single body piece 54 is associated with the internal core member 57, followed by the internal core member 57 being deformed (e.g., by moving the internal core member 57 from a generally linear configuration to an arcuate or annular configuration). So deforming the internal core member 57 causes the frangible bridges 59 to break, thus separating the constituent body elements 58 of the body piece 54. Thereafter, the internal core member 57 may be returned to the generally linear configuration prior to implantation.

While such "single piece" construction may be particularly advantageous for the body elements, it should be understood that one or both of the end pieces (when the proximal end piece is formed of the same material as the body elements, as in FIG. 7) may be integrally formed with an adjacent body element (i.e., formed as a single piece). In such an embodiment, the single piece incorporating the end piece(s) is associated with the internal core member (which may include the end piece(s) being fixedly secured to the internal core member), followed by the internal core member being deformed to break the frangible bridge(s) of the single piece and separate each of the veneer members prior to implantation. It should be understood that bridges may be incorporated into the manufacture of the veneer members of the other embodiments described herein and that this aspect of the present disclosure is not limited to the embodiment of FIGS. 15-19.

Figure 16:
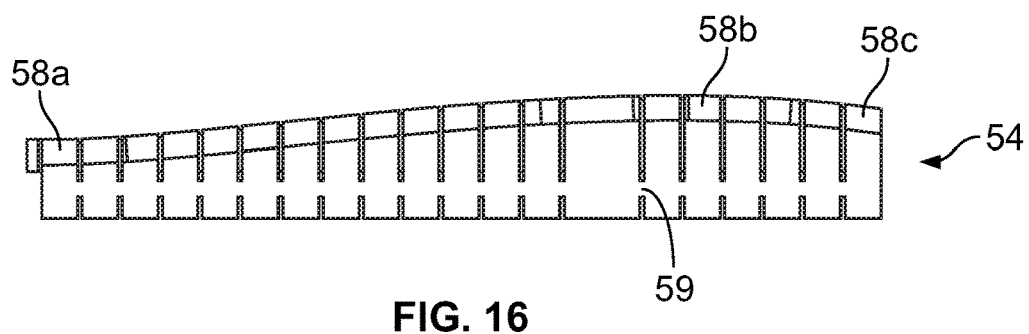
FIG. 16 is a side elevational view of a single body piece of the upper elongated member of FIG. 15.
Figure 18:
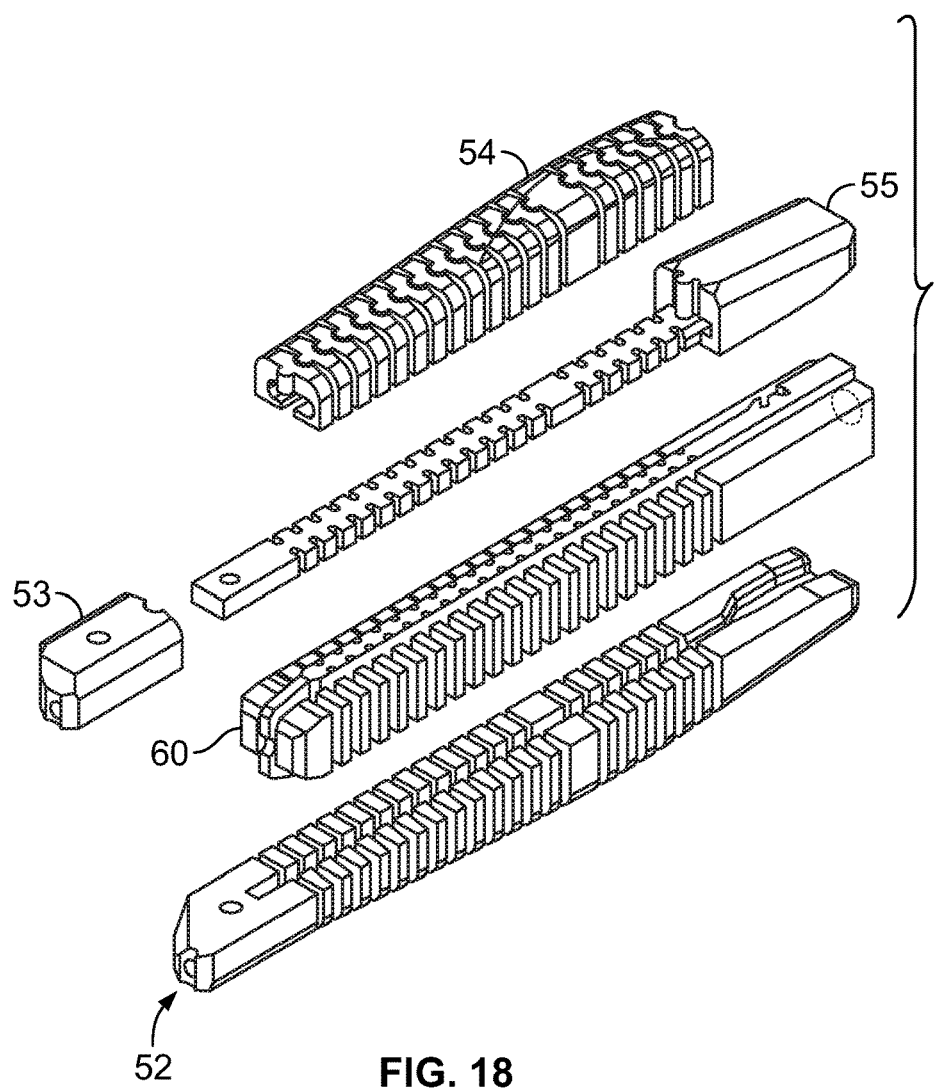
FIG. 18 is a perspective view of the components of a distraction device incorporating the upper elongated member of FIG. 15.
Figure 19:
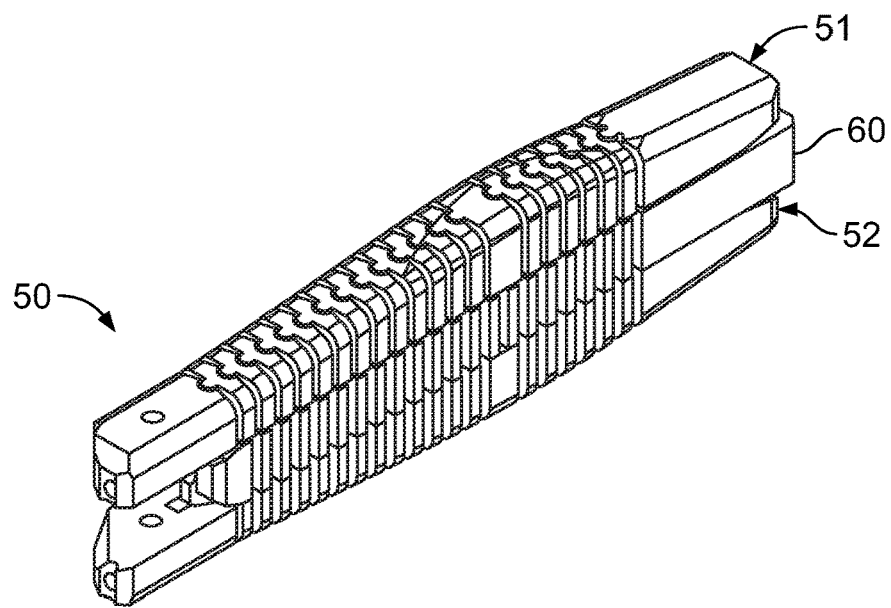
FIG. 19 is a perspective view of the distraction device of claim 18, in an assembled condition.

It may be particularly advantageous for the body elements to be connected together during manufacture if they are differently configured and arranged in a particular orientation. For example, it will be seen that the body elements 58 of FIGS. 15-19 do not have a uniform height or thickness, but that at least two of the body elements 58 have different heights. So providing the body elements 58 with a varying thickness along its length will cause different amounts of distraction along the length of the distraction device 50 (FIG. 19). For instance, as best shown in FIG. 16, the height or thickness of the body elements 58 gradually or incrementally increases from a distal-most body element 58a to a more centrally positioned body element 58b. The height or thickness of the body elements 58 gradually or incrementally decreases from the more centrally positioned, tallest body element 58b to a proximal-most body element 58c. The more distal body elements 58 (including the distal-most body element 58a) may be thinner (shorter) than the more proximal body elements 58 (including the proximal-most body element 58c), which may be thinner (shorter) than more centrally positioned body elements 58 (including the tallest body element 58b). In this case, the increase in the height of the proximal portion of the distraction device 50 will be greater than the augmentation in the height of the distal portion of the distraction device 50, but less than the augmentation in the height of the central portion of the distraction device 50.

Figure 17:
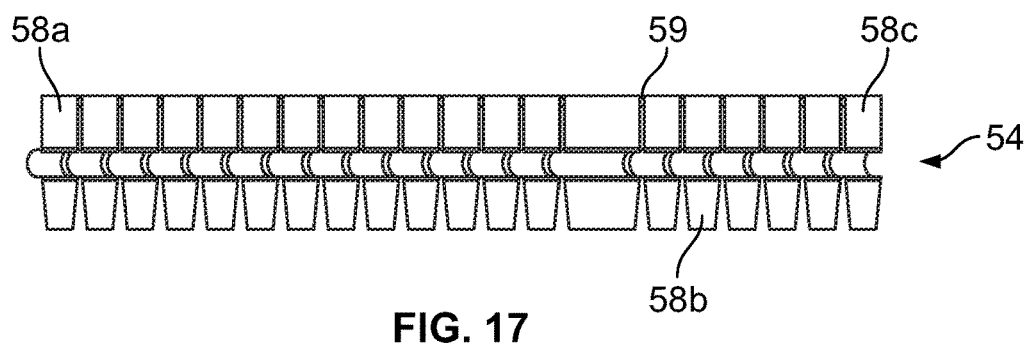
FIG. 17 is a bottom plan view of the single body piece of the upper elongated member of FIG. 15.

It should be understood that the illustrated configuration is merely exemplary and that other configurations (e.g., a configuration in which the more distal body elements are the thickest or tallest of the body elements) are also within the scope of the present disclosure. For example, in addition to (or instead of) body elements having different heights, it is also within the scope of the present disclosure for two or more body elements of an elongated member to have different widths, rather than the body elements having the same width (as best shown in FIG. 17). It should also be understood that the body elements 58 of FIGS. 15-19 may have a uniform height or thickness (and/or varying widths) and that the body elements of the other embodiments described herein may having varying heights or thicknesses (and/or varying widths) without departing from the scope of the present disclosure.

The ability to create a greater increase in height in one region of a distraction device allows for adjustments in the curvature of the spine of a patient. For instance, a collapsed disc in the lumbar region of the spine can result in the loss of the normal lordosis in the lumbar region of the spine. The insertion of upper and/or lower elongated members 51 and 52 of variable thickness/height in a collapsed lumbar disc can restore the lumbar disc to the more normal morphology of a greater height on its anterior region as compared to its posterior region. In such a situation, the upper and/or lower elongated members 51 and 52 may have a greater height at its/their central region between the distal and proximal ends than at either the proximal end or distal end, as in FIGS. 18 and 19. While FIGS. 18 and 19 show upper and lower elongated members 51 and 52 configured as mirror images of each other (which may be particularly advantageous for lordotic correction), with an augmenting elongated member 60 providing substantially uniform separation of the two other elongated members 51 and 52, it should be understood that the upper and lower elongated members 51 and 52 may be configured as other than mirror images of each other.

According to an exemplary implantation method (which may be employed with any of the embodiments described herein), an access port is made through the annulus of a vertebral disc using instruments and endoscopic or minimally invasive procedures generally known to those skilled in the art. The access port may be relatively small (e.g., no larger than the size of a deployment cannula used to implant the distraction device), such that the procedure may be minimally invasive, with the resulting tissue distraction height being greater than the height of the access port. The location of the access port may vary without departing from the scope of the present disclosure, but it is preferred for the location of the access port be chosen so as to decrease the risk of nerve damage. In one embodiment, the access port is positioned so as to facilitate a transforaminal lumbar interbody fusion ("TLIF") approach, but other approaches may also be practiced without departing from the scope of the present disclosure. For example, according to another approach, the access port may be positioned so as to facilitate deployment of the elongated members through Karnbin's triangle, which is defined by the exiting nerve root (the hypotenuse of the triangle), the superior border of the inferior vertebra (the base of the triangle), and the traversing nerve root (the height of the triangle). While this approach results in an access port that is positioned at a different location than in the illustrated TLIF approach, it should be understood that the method of inserting the elongated members so as to define the implant in situ may be substantially the same.

Optionally, all or a portion of the nucleus pulposus is removed and the endplates of the adjacent vertebrae are scraped to cause bleeding and promote the fusion of bone graft material to the vertebral endplates. Sizing paddles or like apparatus, may be slipped through the access port to determine the minimum disc height and the desired final disc height. Based on the minimum and desired final disc height measurement from the sizing paddles, the physician chooses the deployment cannula and distraction device sizes. The maximum outer dimension of the deployment cannula used to deliver the distraction device is preferably similar or slightly smaller in height than the minimum disc height measured. Accounting for the cannula wall thickness and any gap between the cannula and the top-to-bottom height of the first and second elongated members 1 and 2, the first and second elongated members 1 and 2 together are selected so as to be slightly less in height, top to bottom, than the minimum disc height.

Figure 26:
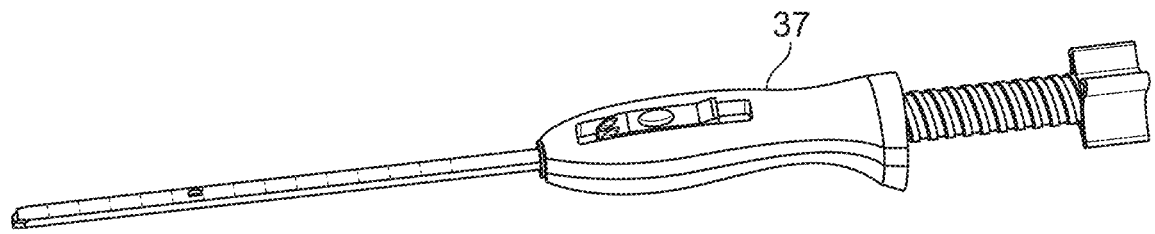
FIG. 26 is a perspective view of the deployment device of FIG. 21.
Figure 30:
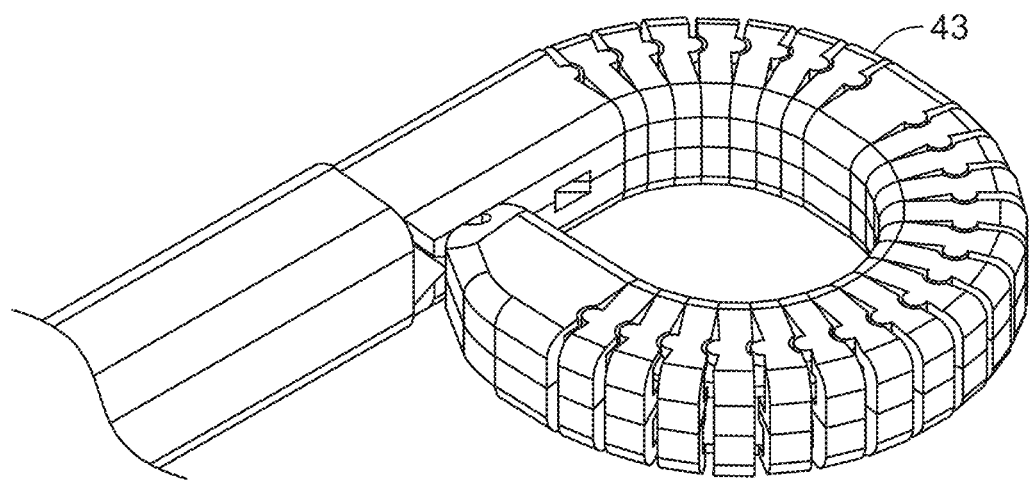
FIG. 30 is a perspective view of an alternative deployment cannula, showing a distraction device in a generally less linear configuration.

FIG. 26 shows an exemplary deployment device 37 that is suitable for such a procedure. The deployment device 37 may be configured and function according to the description of U.S. Pat. No. 9,480,574. Briefly, the deployment device 37 includes a deployment cannula 46 (FIG. 32) in which the elongated members are positioned and constrained into a generally linear configuration, with the first and second elongated members 1 and 2 arranged in a stack distally of the augmenting elongated member 3. The first and second elongated members 1 and 2 are advanced out of the deployment cannula and into position between two tissue layers, such as by operation of a pusher member of the deployment device 37 or by distally advancing the guide member 25, which causes the augmenting elongated member 3 to press against the first and second elongated members 1 and 2 and advance them out of the deployment cannula. Advancement of the first and second elongated members 1 and 2 optionally includes moving them from their generally linear configuration to the generally less linear configuration 43 of FIG. 30. This movement may be automatic (e.g., if the first and second elongated members 1 and 2 are provided with associated shaping members) or may be controlled by an operator or surgeon (e.g., by operating pull wires of the type described in greater detail in U.S. Pat. No. 9,480,574).

Figure 31:
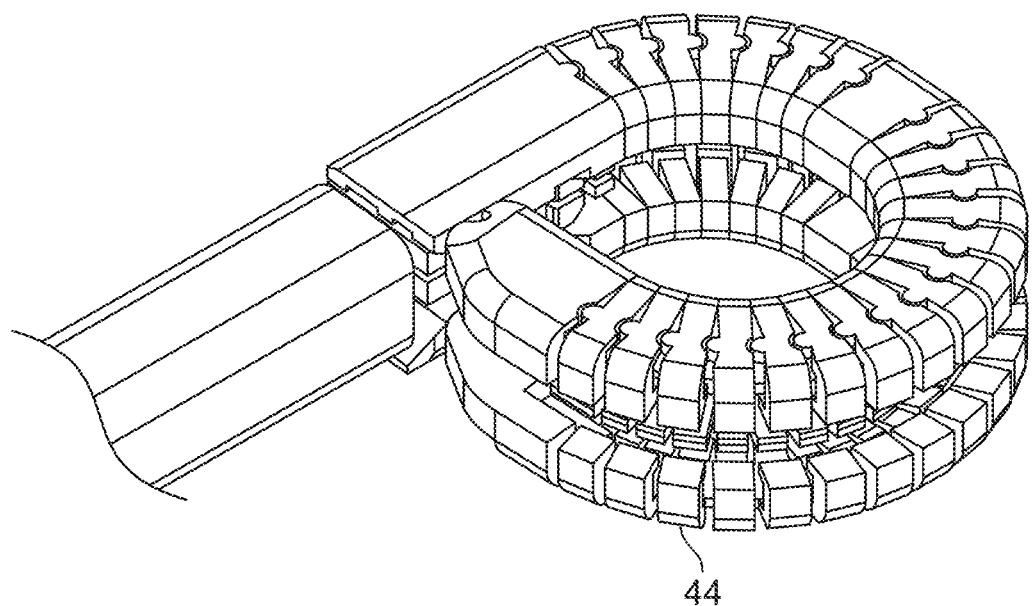
FIG. 31 is a perspective view of the cannula and distraction device of FIG. 30, showing the distraction device in a partially augmented condition.

With the first and second elongated members 1 and 2 positioned outside of the deployment cannula and in the generally less linear configuration, the augmenting elongated member 3 may be advanced out of the deployment cannula and into place between the first and second elongated members 1 and 2. FIG. 31 shows the augmenting elongated member 3 exiting the deployment cannula, which causes the augmenting elongated member 3 to contact and spread apart the first and second elongated members 1 and 2, thereby increasing the dimensional aspect or height of at least a portion of the distraction device. The degree of height increase of the distraction device is dependent upon the height of the augmenting elongated member 3. For instance, a thicker augmenting elongated member (i.e., an augmenting elongated member having a relatively great height) will cause a greater increase in the height of the distraction device than a thinner augmenting elongated member (i.e., an augmenting elongated member having a relatively small height). In embodiments inserted into the disc space to distract adjacent vertebral bodies, the height of the distraction device (which is generally equal to the combined heights of the bodies of the constituent elongated members) is preferably sufficient to restore the disc to its normal height or thereabout, which will depend on the size of the patient and the disc's location in the spinal column. The height of the distraction device can be, for example, from about 5 mm to about 15 mm. More particularly, the height can be from about 7.5 mm to about 13.5 mm, or about 9 mm to about 12 mm and ranges therein. For relatively short individuals or children, the disc size and, consequently, the height of the support structure can be, for example, from about 5 mm to about 7 mm. For relatively tall individuals, the disc height and, consequently, the height of the support structure can be, for example, from about 9 mm to about 15 mm or greater potentially. In other applications, the dimensions (including the heights) of the individual elongated members and the resulting distraction device may vary without departing from the scope of the present disclosure.

In one embodiment, the thickness of the augmenting elongated member 3 can be different along its length to cause different amounts of additional distraction along the length of the distraction device. For instance, the proximal portion of the augmenting member 3 may be thicker (taller) than the distal portion of the augmenting member 3, in which case the increase in the height of the proximal portion of the distraction device will be greater than the augmentation in the height of the distal portion of the device. The ability to create a greater increase in height in one region of a distraction device allows for adjustments in the curvature of the spine of a patient. For instance, a collapsed disc in the lumbar region of the spine can result in the loss of the normal lordosis in the lumbar region of the spine. The insertion of an augmenting elongated member 3 of variable thickness/height between first and second elongated members 1 and 2 deployed in a collapsed lumbar disc can restore the lumbar disc to the more normal morphology of a greater height on its anterior region as compared to its posterior region. In such a situation, the augmenting member 3 may have a greater height at its central region between the distal and proximal ends than at either the proximal end or distal end. Rather than (or in addition to) the augmenting member 3 having a varying thickness, one or both of the first and second elongated members 1 and 2 may have a varying thickness (as in FIGS. 15-19), if lordotic correction is required. Alternatively, the elongated members may be configured to combine to form a distraction device having a generally uniform height or dimensional aspect for uniform distraction of a pair of tissue layers.

Preferably, once augmented, the height or dimensional aspect of the distraction device is fixed and is not adjustable or variable, while the augmenting member 3 is preferably fixed in position between the first and second elongated members 1 and 2 and not removable. For example, as described above, the elongated members may be provided with mating formations that prevent the first and second elongated members 1 and 2 from separating from the augmenting elongated member 3. Prior to full insertion of the augmenting elongated member 3, it may be moved proximally and at least partially out of position between the first and second elongated members 1 and 2 for repositioning and readjustment, as necessary. If the augmenting elongated member 3 is provided with an associated guide member 25, the guide member 25 may be moved proximally to withdraw the augmenting elongated member 3 from between the first and second elongated members 1 and 2.

Figure 32:
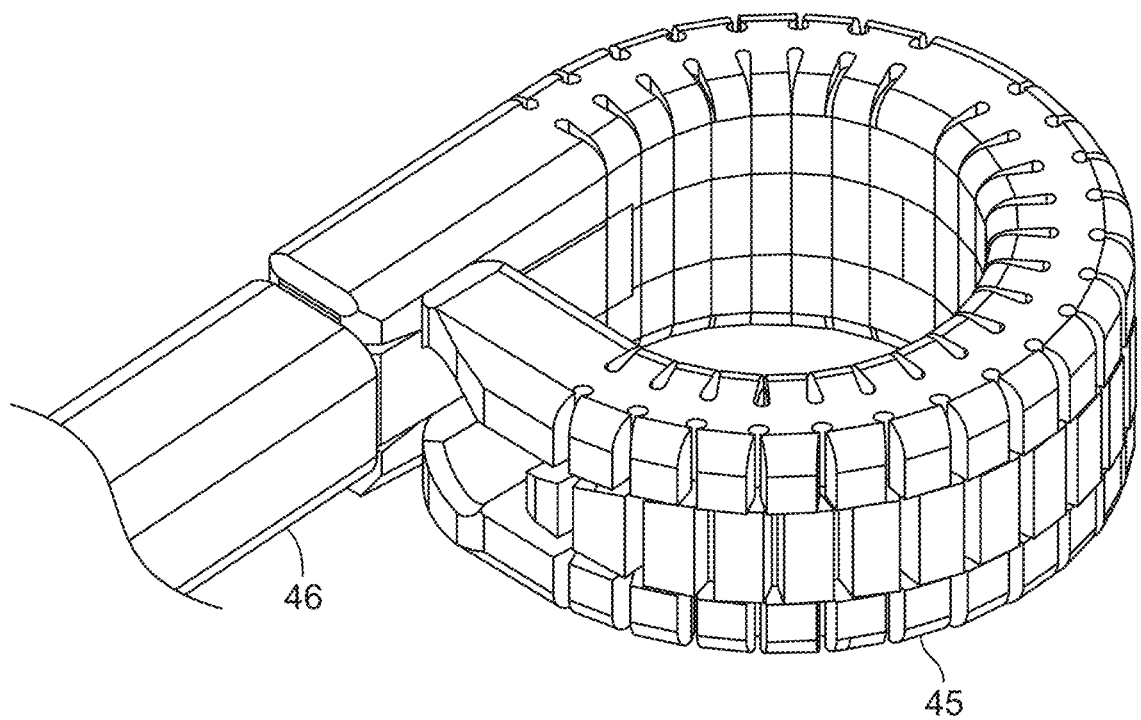
FIG. 32 is a perspective view of the cannula and distraction device of FIG. 31, showing the distraction device in a fully augmented condition.

FIG. 31 shows the augmenting elongated member 3 in a partially inserted condition 44, while FIG. 32 shows the augmenting elongated member 3 in a fully inserted condition 45. As shown in FIG. 32, the augmenting elongated member 3 may be shorter or less elongated than the first and second elongated members 1 and 2, thereby defining a window in the fully assembled distraction device. The function of the window will be described in greater detail herein.

Figure 28:
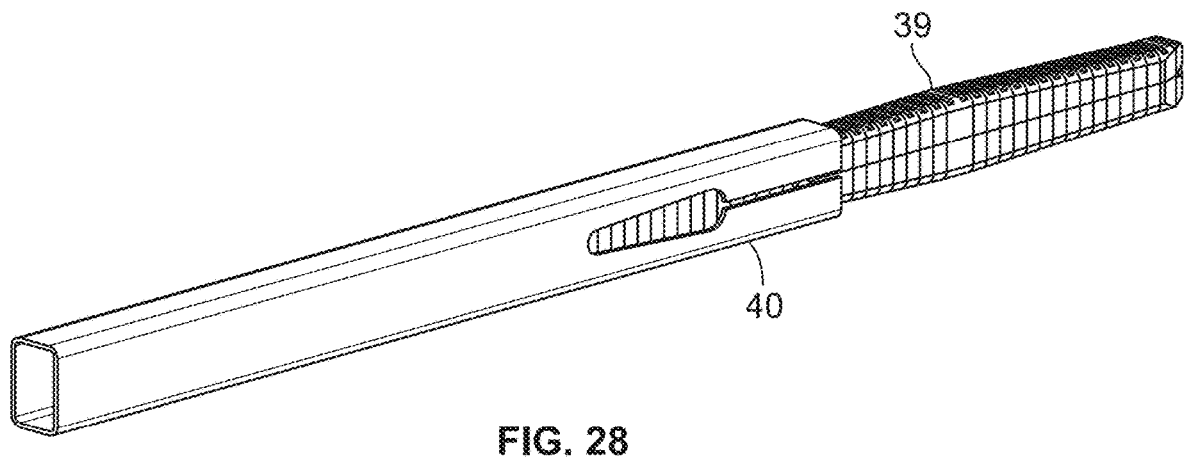
FIGS. 28 and 29 are perspectives view of the cannula of FIG. 27, with components of the distraction device partially positioned outside of the cannula.
Figure 29:
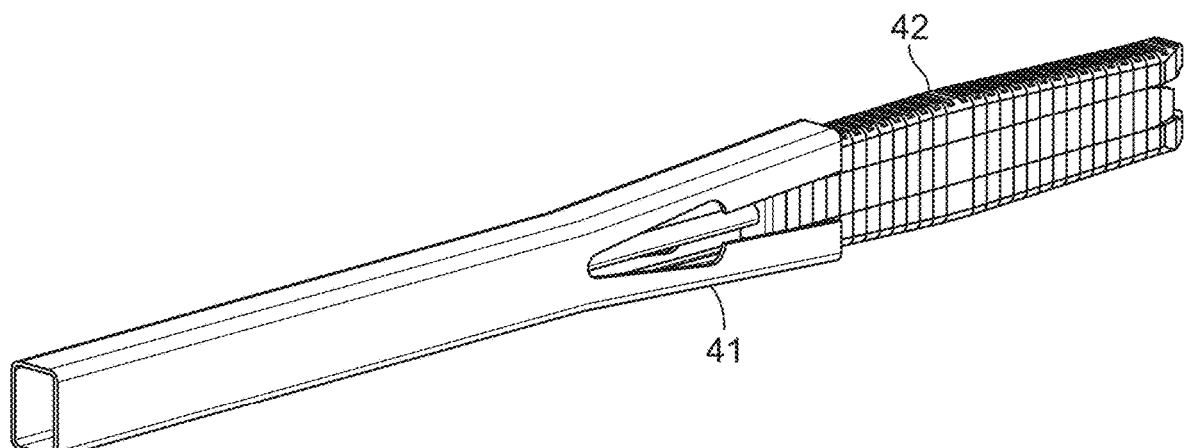

FIGS. 27-29 illustrate insertion of the distraction device using a modified deployment cannula 38. In particular, the deployment cannula 38 includes a deformable distal end, which is configured to change between an initial configuration (generally identified in FIG. 28 at 40) and an expanded or deformed configuration (generally identified in FIG. 29 at 41). In the illustrated embodiment, the distal end of the deployment cannula 38 has a split design or configuration, which allows a first or upper portion of the distal end of the deployment cannula 38 to resiliently flex away from a second or lower portion of the distal end of the deployment cannula 38. The distal end of the deployment cannula 38 retains its initial configuration with the first and second elongated members 1 and 2 partially advanced out of the deployment cannula 38 (as generally identified in FIG. 28 at 39), before moving to its deformed configuration when the augmenting elongated member 3 is at least partially inserted between the first and second elongated members 1 and 2 with the first and second elongated members 1 and 2 still partially positioned within the deployment cannula 38 (as generally identified in FIG. 29 at 42). FIGS. 28 and 29 show the elongated members retaining their generally linear configuration (which would be the case for an embodiment in which shaping members are omitted and replaced with some other shaping mechanism, such as pull wires), but it should be understood that the portions of the first and second elongated members 1 and 2 positioned outside of the deployment cannula 38 will typically move from their generally linear configuration to a generally less linear configuration upon exiting the deployment cannula 38.

Rather than the opposing portions of the distal end of the deployment cannula 38 freely pivoting away from each other, they are preferably deformed outwardly against a resilient force that tends to bring the opposing portions back to their initial configuration. Such a resilient force helps to maintain proper position of the elongated members during assembly of the distraction device and ensure that the augmenting elongated member 3 is successfully engaged by the first and second elongated member 1 and 2 during insertion. However, while the illustrated configuration may be preferred, it should be understood that the deformability of the distal end of the deployment cannula may be imparted by a different mechanism without departing from the scope of the present disclosure. It should also be understood that a deployment cannula with a deformable distal end may be used in combination with any suitable distraction device and is not limited to use in combination with the distraction devices described herein.

As described above, the augmenting elongated member 3 may be provided with an associated guide member 25, with the combined augmenting elongated member and guide member being generally identified at 26 in FIG. 20. FIGS. 21-25 illustrate an exemplary method in which the guide member 25 is used to inject a filler material into an interior of a deployed distraction device, followed by removal of the guide member 25 from the distraction device. In particular, the distraction device is formed with the guide member 25 attached to the augmenting elongated member 3, with at least a portion of the guide member 25 remaining within the deployment cannula during implantation. Once the deployment is completed, the deployment device (identified in FIG. 21 at 27 in a condition in which a pusher member has been advanced to deploy the elongated members) is disconnected from the distraction device 28 (including the guide member 25) and moved proximally (as indicated at 29 in FIG. 21) to completely dissociate the deployment device from the distraction device 28.

Figure 22:
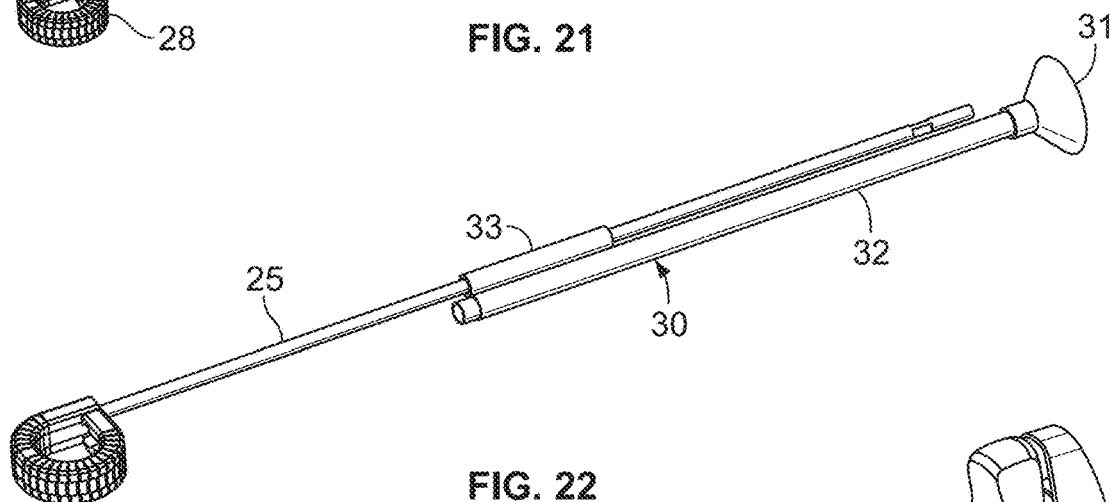
FIG. 22 is a bottom perspective view of the distraction device of FIG. 20, showing an injection aid being moved toward the distraction device, along the guide member.
Figure 23:
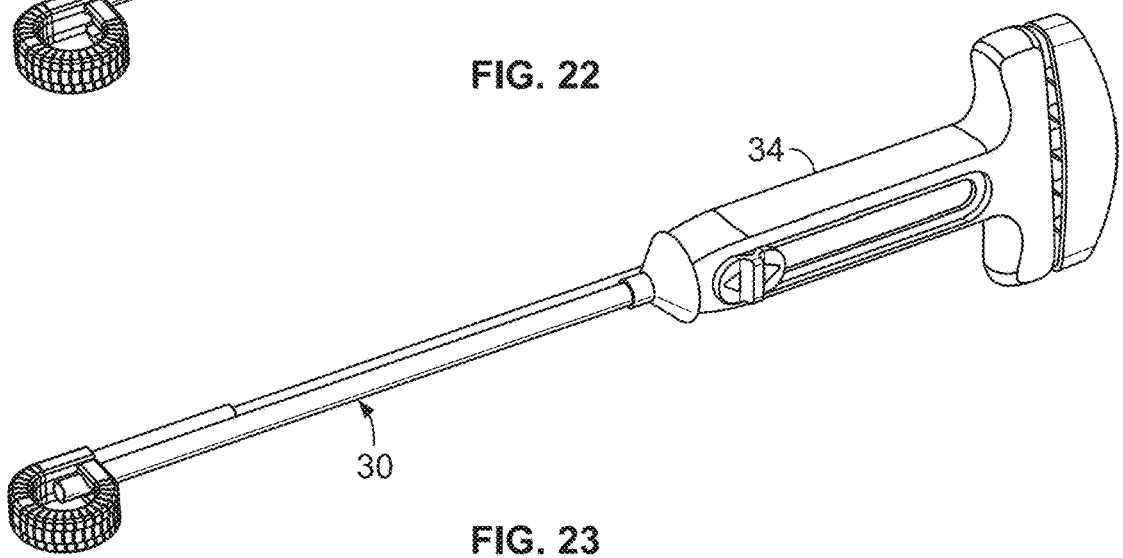
FIG. 23 is a bottom perspective view of the distraction device and injection aid of FIG. 22, with an injector device received by the injection aid.

The guide member 25 serves as a guide for an injection aid 30, which is shown in FIG. 22. The injection aid 30 includes a follower member or guiding tube 33 and a funnel member or guide port 32. The follower member 33 is associable with the guide member 25 to allow movement of the injection aid 30 along at least a portion of the length of the guide member 25. For example, the follower member 33 may be configured as a tube that receives the guide member 25 for sliding movement of the injection aid 30 along the guide member 25 toward and away from the distraction device 28. As for the funnel member 32, it defines a lumen and extends between a proximal end or funnel 31 configured to accommodate at least a portion of an injection device 34 (FIG. 23) and a distal end. In addition to allowing for movement of the injection aid 30 along the guide member 25, the follower member 33 also serves to align the distal end of the funnel member 32 with a window defined in the distraction device 28. To that end, it may be advantageous for the follower member 33 to be configured to have a keyed relationship with the guide member 25, such that the follower member 33 may only be associated with the guide member 25 in one orientation that properly aligns the funnel member 32 and the window.

The injection aid 30 is moved along the guide member 25 to place the distal end of the funnel member 32 adjacent to the window of the distraction device 28, at least partially inside of the window, or in the interior of the distraction device 28 via the window. With the distal end of the funnel member 32 so positioned, an injector device 34 (which, in one embodiment, is configured as described in U.S. Patent Application Publication No. 2016/0228261, which is hereby incorporated herein by reference) is partially advanced into the lumen of the funnel member 32. The injector device 34 is then used to introduce a filler material or bone graft material into the interior of the distraction device 28.

Figure 24:
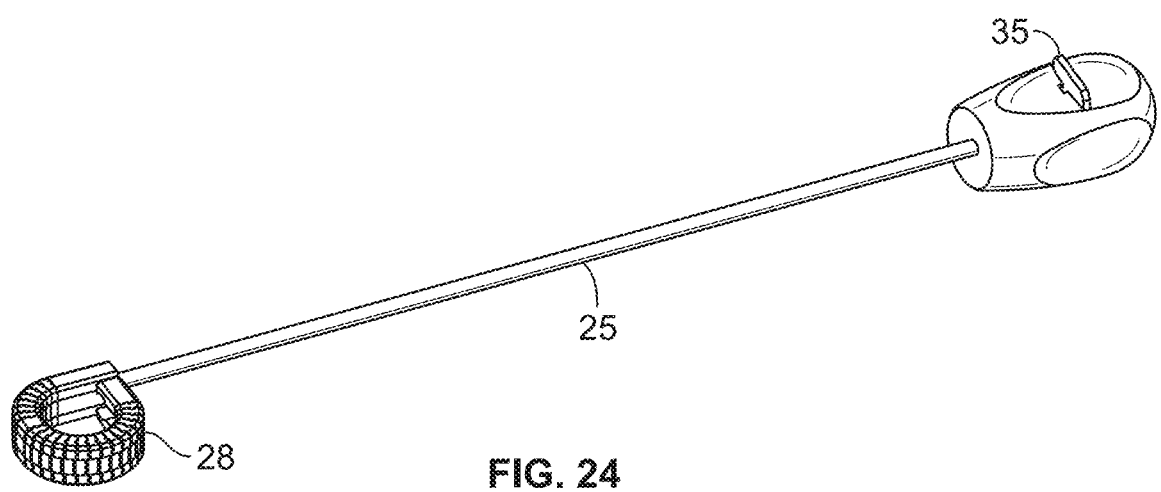
FIG. 24 is a bottom perspective view of the distraction device and guide member of FIG. 20, with a handle member associated with the guide member for removal of the guide member from the distraction device.
Figure 25:
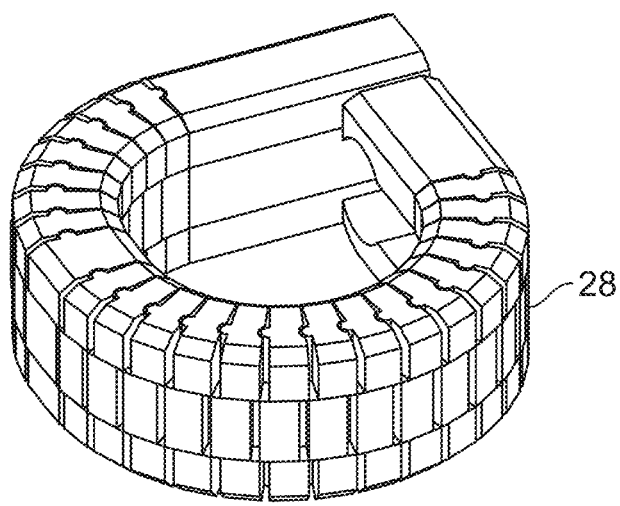
FIG. 25 is a bottom perspective view of the distraction device of FIG. 24, with the guide member removed therefrom.

Upon completion of that step, the injector device 34 and injection aid 30 may be moved proximally away from the distraction device 28 to completely dissociate the injection aid 30 and the injector device 34 from the distraction device 28 and the guide member 25. The guide member 25 may then be removed from the distraction device 28. In one embodiment, a proximal portion of the guide member 25 includes a formation or recess 36 (FIG. 20) configured to accommodate a handle member 35, as shown in FIG. 24. With the handle member 35 attached to the guide member 25, the handle member 35 may be manipulated (e.g., to cause the guide member 25 to rotate about its central axis) to disconnect the guide member 25 from the distraction device 28, leaving only the distraction device 28 between the tissue layers (FIG. 25) to complete the implant deployment operation. It should be understood that the guide member 25 and associated method of use may be used in combination with other distraction members having an interior to be at least partially filled with a filler material and is not limited to use in combination with distraction devices of the type described herein.

Following removal of the guide member 25, the access port may be closed, along with any other access points opened to reach the disc space. Additional details of a suitable implantation method may be found in U.S. Pat. No. 9,480,574.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A tissue distraction device comprising:
a first elongated member and a second elongated member,
an augmenting elongated member configured to cooperatively interact with the first elongated member and the second elongated member to increase a dimensional aspect of the tissue distraction device, wherein each of the first elongated member and the second elongated member comprises a hybrid structure comprised of an elongated internal core member and a veneer at least partially surrounding the elongated internal core member and spaced along the length of the elongated internal core member, wherein the elongated internal core member and the veneer comprise different materials, wherein the elongated internal core member is sufficiently flexible to change between a generally linear configuration and a generally less linear configuration, wherein the elongated internal core member comprises a polymer material, and the veneer is substantially formed of a generally rigid material, wherein the veneer comprises a metallic material.

2. The tissue distraction device of claim 1, wherein the elongated internal core member is substantially formed of polyetheretherketone.

3. The tissue distraction device of claim 1, wherein said generally rigid material comprises a titanium material.

4. The tissue distraction device of claim 1, wherein at least a portion of an outer surface of the veneer has a rough, porous surface.

5. The tissue distraction device of claim 1, wherein the first elongated member and the second elongated member are configured to be in a generally annular configuration when the elongated internal core members are in said generally less linear configuration.

6. The tissue distraction device of claim 1, further comprising a shaping member, wherein the shaping member is configured to automatically move the tissue distraction device from the generally linear configuration to the generally less linear configuration.

7. The tissue distraction device of claim 6, wherein the shaping member is fully embedded within the augmenting elongated member.

8. The tissue distraction device of claim 1, wherein the augmenting elongated member comprises a shape memory material and is configured to move the tissue distraction device from the generally linear configuration to the generally less linear configuration.

9. The tissue distraction device of claim 1, wherein the second elongated member is a mirror image of the first elongated member.

10. The tissue distraction device of claim 1, wherein the first elongated member comprises an inclined surface on an upper surface of a distal end to ease passage of the first elongated member through tissue.

11. The tissue distraction device of claim 10, wherein the second elongated member comprises an inclined surface on a lower surface of a distal end to ease passage of the second elongated member through tissue.

12. The tissue distraction device of claim 1, wherein the first elongated member and the second elongated member comprise a slot extending along a portion of their lengths to receive a raised rib of the augmenting elongated member.

13. The tissue distraction device of claim 1, wherein the first elongated member and the second elongated member comprise a slot with a relatively narrow necked-down portion to receive a T-shaped raised rib of the augmenting elongated member.

14. The tissue distraction device of claim 1, further comprising a shape memory rod configured to deflect the augmenting elongated member.

15. The tissue distraction device of claim 14, wherein the shape memory rod remains in the augmenting elongated member following implantation of the tissue distraction device.

16. The tissue distraction device of claim 1, wherein the veneer extends along at least a portion of an upper surface and lateral surfaces of the first elongated member.

17. The tissue distraction device of claim 16, wherein the veneer extends along at least a portion of a lower surface and lateral surfaces of the second elongated member.

18. The tissue distraction device of claim 1, wherein the augmenting elongated member is configured to be at least partially inserted between the first elongated member and the second elongated member.

19. The tissue distraction device of claim 6, wherein the augmenting elongated member comprises the shaping member.

20. The tissue distraction device of claim 1, wherein the augmenting elongated member is shorter or less elongated than the first elongated member.

21. The tissue distraction device of claim 20, wherein the augmenting elongated member is shorter or less elongated than the second elongated member.

* * * * *